United States Patent
Forsyth

(10) Patent No.: US 10,190,113 B2
(45) Date of Patent: Jan. 29, 2019

(54) METHODS AND COMPOSITIONS FOR SEGREGATING TARGET NUCLEIC ACID FROM MIXED NUCLEIC ACID SAMPLES

(71) Applicant: FLIR DETECTION, INC., Stillwater, OK (US)

(72) Inventor: Roger Allyn Forsyth, San Diego, CA (US)

(73) Assignee: FLIR DETECTION, INC., Stillwater, OK (US)

( * ) Notice: Subject to any disclaimer, the term of this patent is extended or adjusted under 35 U.S.C. 154(b) by 0 days.

(21) Appl. No.: 15/782,277

(22) Filed: Oct. 12, 2017

(65) Prior Publication Data

US 2018/0112206 A1   Apr. 26, 2018

Related U.S. Application Data

(60) Continuation of application No. 14/591,291, filed on Jan. 7, 2015, now Pat. No. 9,790,486, which is a continuation of application No. 13/958,125, filed on Aug. 2, 2013, now Pat. No. 8,940,296, which is a division of application No. 13/533,489, filed on Jun. 26, 2012, now Pat. No. 8,927,218.

(60) Provisional application No. 61/501,569, filed on Jun. 27, 2011.

(51) Int. Cl.

| | |
|---|---|
| C12Q 1/68 | (2018.01) |
| C12N 15/10 | (2006.01) |
| C12Q 1/6806 | (2018.01) |
| C12Q 1/6844 | (2018.01) |
| C12Q 1/06 | (2006.01) |
| C12Q 1/34 | (2006.01) |
| A61K 38/46 | (2006.01) |

(52) U.S. Cl.
CPC .......... *C12N 15/1003* (2013.01); *C12Q 1/06* (2013.01); *C12Q 1/6806* (2013.01); *C12Q 1/6844* (2013.01); *A61K 38/46* (2013.01); *A61K 38/465* (2013.01); *C12Q 1/34* (2013.01); *C12Q 2521/301* (2013.01); *C12Q 2527/125* (2013.01)

(58) Field of Classification Search
None
See application file for complete search history.

(56) References Cited

U.S. PATENT DOCUMENTS

| | | |
|---|---|---|
| 6,168,918 B1 | 1/2001 | Satishchandran et al. |
| 6,713,279 B1 | 3/2004 | Short |
| 8,927,218 B2 | 1/2015 | Forsyth |
| 8,940,296 B2 | 1/2015 | Forsyth |
| 9,790,486 B2 | 10/2017 | Forsyth |
| 2002/0197639 A1 | 12/2002 | Shia et al. |
| 2004/0180372 A1 | 9/2004 | Nelson |
| 2005/0123944 A1 | 6/2005 | Neely et al. |
| 2005/0272065 A1 | 12/2005 | Lakey et al. |
| 2008/0254453 A1 | 10/2008 | Shapero et al. |
| 2009/0252707 A1 | 10/2009 | Krohn et al. |
| 2009/0298080 A1 | 12/2009 | Hanna et al. |
| 2010/0081174 A1 | 4/2010 | Dunn |
| 2010/0167942 A1 | 7/2010 | Zheng et al. |

FOREIGN PATENT DOCUMENTS

| | | |
|---|---|---|
| WO | WO 99/40222 A1 | 8/1999 |
| WO | WO 03/025118 A2 | 3/2003 |
| WO | WO 2005/012575 A1 | 2/2005 |
| WO | WO 2006/074233 A2 | 7/2006 |
| WO | WO 2008/097467 A1 | 8/2008 |
| WO | WO 2013/003376 A2 | 1/2013 |

OTHER PUBLICATIONS

De La Campa, A.G., et al., "Proteins encoded by the DpnI restriction gene cassette. Hyperproduction and characterization of the DpnI endonuclease." *J. Biol. Chem.*, 263(29):14696-14702, American Society for Biochemistry and Molecular Biology, 1988.

Erlanger, B.F. and Beiser, S.M., "Antibodies Specific for Ribonucleosides and Ribonucleotides and Their Reaction with DNA," *Proc. Natl Acad. Sci. U.S.A.*, 52:68-74, United States National Academy of Sciences, 1964.

Itoh, K., et al., "Preparation of a monoclonal antibody specific for 1-methyladenosine and its application for the detection of elevated levels of 1-methyladenosine in urines from cancer patients," *Jpn J. Cancer Res.*, 79:1130-1138, Japanese Cancer Association, 1988.

Kempenaers, M., et al., "New archaeal methyltransferases forming 1-methyladenosine or 1-methyladenosine and 1-methylguanosine at position 9 of tRNA," *Nucleic Acids Res.*, 38:6533-6543, Oxford University Press, 2010.

Marinus, M.G. and Casadesus, J., "Roles of DNA adenine methylation in host-pathogen interactions: mismatch repair, transcriptional regulation, and more," *FEMS Microbiol. Rev.*, 33:488-503, Elsevier Science Publishers, 2009.

Ratel, D., et al., "N6-methyladenine: the other methylated base of DNA," *Bioessays*, 28:309-315, ICSU Press by Cambridge University Press, 2006.

Reynaud, C., et al., "Monitoring of urinary excretion of modified nucleosides in cancer patients using a set of six monoclonal antibodies," *Cancer Lett.*, 61(3):255-262, Elsevier Scientific Publishers, 1991.

(Continued)

*Primary Examiner* — James Martinell
(74) *Attorney, Agent, or Firm* — Sterne, Kessler, Goldstein & Fox P.L.L.C.

(57) ABSTRACT

The invention provides methods, compositions and kits for segregating a target nucleic acid from a mixed nucleic acid sample. The methods, compositions and kits comprise a non-processive endonuclease (e.g., a restriction enzyme) or an antibody that binds the target nucleic acid (e.g., has methylation specificity). The mixed nucleic acid sample can comprise prokaryotic and eukaryotic nucleic acid and/or nucleic acid from more than one prokaryotic or eukaryotic organisms.

17 Claims, 24 Drawing Sheets

Specification includes a Sequence Listing.

(56) References Cited

OTHER PUBLICATIONS

Sachse, S., et al., "Truncated human cytidylate-phosphate-deoxyguanylate-binding protein for improved nucleic acid amplification technique-based detection of bacterial species in human samples," *J. Clin. Microbiol.*, 47:1050-1057, American Society for Microbiology, 2009.

Störl, H.J., et al., "Immunochemical detection of $N^6$-methyladenine in DNA," *Biochim. Biophys. Acta*, 564(1): 23-30, Elsevier/North-Holland Biomedical Press, 1979.

Wion, D. and Casadesús, J., "$N^6$-methyl-adenine: an epigenetic signal for DNA-protein interactions," *Nat. Rev. Microbiol.*, 4(3):183-192, Nature Publishing Group, 2006.

Xiao, R. and Moore, D.D., "DamIP: using mutant DNA adenine methyltransferase to study DNA-protein interactions in vivo." *Curr. Protoc. Mol. Biol.*, 21:1-13, Greene Pub. Associates Wiley-Interscience, 2011.

Bellamy, S.R.W., et al., "Differences between $Ca^{2+}$ and $Mg^{2+}$ in DNA binding and release by the SfiI restriction endonuclease: implications for DNA looping," *Nucleic Acids Research* 37:5443-5453, Oxford University Press, England, 2009.

Keum, J.-W. and Bermudez, H., "Enhanced resistance of DNA nanostructures to enzymatic digestion," *Chem. Commun.* 45:7036-7038, The Royal Society of Chemistry, England, 2009.

Nakahara, T., et al., "Human Papillomavirus Type 16 E1^E4 Contributes to Multiple Facets of the Papillovirus Life Cycle," *J. Virol.* 79:13150-13165, American Society for Microbiology, United States, 2005.

Robinson, D., et al., "Restriction Endonucleases," in *Molecular Biology Problem Solver: A Laboratory Guide*, Chapter 9, Gerstein, A.S., ed., pp. 244-266, Wiley-Liss, Inc., Wilmington, United States, 2001.

Van Steensel laboratory, "Isolation of methylated regions," Technical paper retrieved from the internet on Nov. 21, 2012 at url:research.nki.nl/vansteensellab/misc_files/Isolation_of_methylated_regions_20061006.pdf, dated Jun. 10, 2006, pp. 1-3.

Xiao, R., et al., "DamIP: A novel method to identify DNA binding sites in vivo," *Nuclear Receptor Signaling* 8:1-6, Nuclear Receptor Signaling Atlas, United States, 2010.

Xu, S.-Y. and Schildkraut, I., "Isolation of BamHI Variants with Reduced Cleavage Activities," *J. Biol. Chem*. 266:4425-4429, American Society for Biochemistry and Molecular Biology, United States, 1991.

International Search Report and Written Opinion for Int'l Appl. No. PCT/US2012/044256, international filing date: Jun. 26, 2012, dated Dec. 10, 2012 from the U.S. Patent and Trademark Office, Alexandria, Virginia.

Ishiwata, S., et al., "Comparison of Serum and Urinary Levels of Modified Nucleoside, 1-Methyladenosine, in Cancer Patients Using a Monoclonal Antibody-Based Inhibition ELISA," *Tohoku J. Exp. Med.*, 176:61-68, Tohoku University Medical Press, Sendai, Japan, 1995.

International Search Report and Written Opinion for Int'l Appl. No. PCT/US2012/071364, international filing date: Dec. 21, 2012, dated Aug. 27, 2013 from the U.S. Patent and Trademark Office, Alexandria, Virginia.

Rigas, B., et al., "Rapid plasmid library screening using RecA-coated biotinylated probes," *Proc. Natl. Acad. Sci. USA* 83:9591-9595, National Academy of Sciences Washington, DC, 1986.

Non-Final Office Action dated Dec. 20, 2013 for U.S. Appl. No. 13/533,489, filed Jun. 26, 2012, inventor: Roger Allyn Forsyth.

Ahern, H. "Biochemical, Reagents Kits Offer Scientists Good Return on Investment," *The Scientist*, 9(15):20, The Scientist, Inc., Philadelphia, PA, 1995.

International Preliminary Report on Patentability for Int'l Appl. No. PCT/US2012/0171364, international filing date: Dec. 21, 2012, dated Dec. 31, 2014, International Bureau of WIPO, Geneva, Switzerland.

International Preliminary Report on Patentability for Int'l Appl. No. PCT/US2012/044256, international filing date: Jun. 26, 2012, dated Jan. 7, 2015, International Bureau of WIPO, Geneva, Switzerland.

Extended European Search Report for EP Appl. No. 1284001.1, dated Jan. 29, 2015, European Patent Office, Munich, Germany.

Seawell, P.C., et al., "Binding of T4 endonuclease V to deoxyribonucleic acid irradiated with ultraviolet light," *Biochemistry*, 19(8):1685-1691, ACS Publications, Washington, DC, 1980.

Dorvel, B., et al., "Analyzing the forces binding a restriction endonuclease to DNA using a synthetic nanopore," *Nucleic Acids Research*, 37(12):4170-4179, Oxford Journals, Oxford, United Kingdom, 2009.

Non-Final Office Action dated Nov. 2, 2016 for U.S. Appl. No. 14/591,291, filed Jan. 7, 2015, inventor: Roger Allyn Forsyth.

FIG. 1A

```
GATCCCTGACTTGAGCAGTAACTAGC GCGGCCGC GCAGGATAACAAGTCACACTGAG
    GGACTGAACTCGTCATTGATCG CGCCGGCG CGTCCTATTGTTCAGTGTGACTC CTAG
overhang       Primer#1            NotI            Primer#2       overhang
```

FIG. 1B

| Name | Sequence | Purpose |
|---|---|---|
| Linker-Sense | 5'GATCCCTGACTTGAGCAGTAACTAGCGCGGCCGCGCAGG ATAACAAGTCACACTGAG-3' | Ligates onto GATC 5' overhangs creating a circular molecule resistant to exonucleases |
| Linker-Anti | 5'GATCCTCAGTGTGACTTGTTATCCTGCGCGGCCGCGCTAG TTACTGCTCAAGTCAGG-3' | Ligates onto GATC 5' overhangs creating a circular molecule resistant to exonucleases |
| Linker-Sense-4nt-2 | 5'GCTAGTTACTGCTGAAGTCAGG-3' | Ligates to GATC 5' ends. Creates 4 nucleotide overhang to block ExoIII |
| Linker-Anti-4nt-2 | 5'GATCGGACTGAACTCGTCATTGATCGAAGG-3' | Ligates to GATC 5' ends. Creates 4 nucleotide overhang to block ExoIII |
| Linker-Sense-4nt-3 | 5'TACAAGGCTAGTTACTGCTCAAGTCAGG-3' | Ligates to GATC 5' ends, leaves a 4 nucleotide overhang that blocks ExoII |
| Linker-Anti-4nt-3 | 5'GATCGGACTGAACTCGTCATTGATCGGAACATAAGG-3' | Ligates to GATC 5' ends, leaves a 4 nucleotide overhang that blocks ExoII |
| Primer #1 | 5'GCTAGTTACTGCTCAAGTCAGG-3' | Amplifies templates containing above adaptors |
| Primer #2 | 5'GCAGGATAACAAGTCACACTGAG-3' | Amplifies templates containing above adaptors |

FIG. 16

| Organism | Mass ratio in the mix | Pre-Enrichment Sequence reads | Pre-Enrichment % representation | Post-Enrichment Sequence reads | Post-Enrichment % representation | Fold enrichment |
|---|---|---|---|---|---|---|
| Bacillus atrophaeus | 100 | 46,615,091 | 96.66 | 51,379,233 | 58.92 | 0.60 |
| Pseudomonas aeruginosa | 10 | 127,312 | 0.26 | 440,008 | 0.5 | 1.92 |
| E. coli | 1 | 1,291,461 | 2.68 | 33,131,196 | 37.99 | 14.17 |
| AcNVP | 10 | 46,336 | 0.1 | 78,971 | 0.09 | 0.9 |
| phage lambda | 1 | 146,123 | 0.3 | 2,172,151 | 2.49 | 8.3 |
| | | 48,226,323 | 100 | 84,950,437 | | |

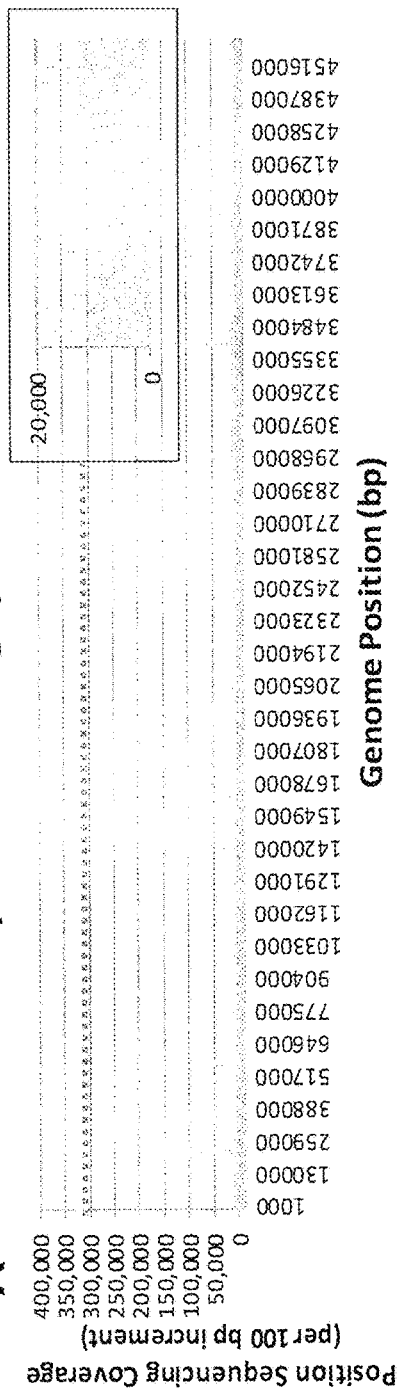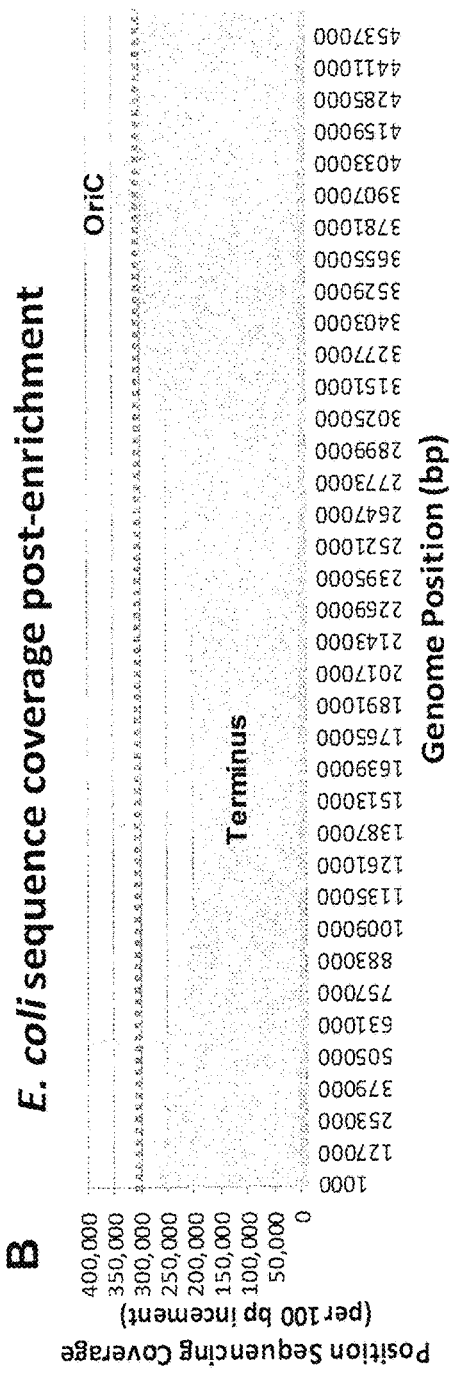
FIG. 17

SEQUENCE LISTING

```
<160> NUMBER OF SEQ ID NOS: 9

<210> SEQ ID NO 1
<211> LENGTH: 114
<212> TYPE: DNA
<213> ORGANISM: Artificial Sequence
<220> FEATURE:
<223> OTHER INFORMATION: synthetic adaptor
<220> FEATURE:
<221> NAME/KEY: misc_feature
<222> LOCATION: (1)..(4)
<223> OTHER INFORMATION: overhang
<220> FEATURE:
<221> NAME/KEY: misc_feature
<222> LOCATION: (111)..(114)
<223> OTHER INFORMATION: overhang

<400> SEQUENCE: 1
gatccctgac ttgagcagta actagcgcgg ccgcgcagga taacaagtca cactgaggga      60
ctgaactcgt cattgatcgc gccggcgcgt cctattgttc agtgtgactc ctag           114

<210> SEQ ID NO 2
<211> LENGTH: 57
<212> TYPE: DNA
<213> ORGANISM: Artificial Sequence
<220> FEATURE:
<223> OTHER INFORMATION: Linker-Sense

<400> SEQUENCE: 2
gatccctgac ttgagcagta actagcgcgg ccgcgcagga taacaagtca cactgag        57

<210> SEQ ID NO 3
<211> LENGTH: 57
<212> TYPE: DNA
<213> ORGANISM: Artificial Sequence
<220> FEATURE:
<223> OTHER INFORMATION: Linker-Anti

<400> SEQUENCE: 3
gatcctcagt gtgacttgtt atcctgcgcg gccgcgctag ttactgctca agtcagg        57
```

```
<210> SEQ ID NO 4
<211> LENGTH: 22
<212> TYPE: DNA
<213> ORGANISM: Artificial Sequence
<220> FEATURE:
<223> OTHER INFORMATION: Linker-Sense -4nt-2

<400> SEQUENCE: 4
gctagttact gctcaagtca gg                                          22

<210> SEQ ID NO 5
<211> LENGTH: 30
<212> TYPE: DNA
<213> ORGANISM: Artificial Sequence
<220> FEATURE:
<223> OTHER INFORMATION: Linker-Anti-4nt-2

<400> SEQUENCE: 5
gatcggactg aactcgtcat tgatcgaagg                                  30

<210> SEQ ID NO 6
<211> LENGTH: 28
<212> TYPE: DNA
<213> ORGANISM: Artificial Sequence
<220> FEATURE:
<223> OTHER INFORMATION: Linker-Sense-4nt-3

<400> SEQUENCE: 6
tacaaggcta gttactgctc aagtcagg                                    28

<210> SEQ ID NO 7
<211> LENGTH: 36
<212> TYPE: DNA
<213> ORGANISM: Artificial Sequence
<220> FEATURE:
<223> OTHER INFORMATION: Linker-Anti-4nt-3

<400> SEQUENCE: 7
gatcggactg aactcgtcat tgatcggaac ataagg                           36

<210> SEQ ID NO 8
<211> LENGTH: 22
<212> TYPE: DNA
<213> ORGANISM: Artificial Sequence
<220> FEATURE:
<223> OTHER INFORMATION: Primer 1

<400> SEQUENCE: 8
gctagttact gctcaagtca gg                                          22

<210> SEQ ID NO 9
<211> LENGTH: 23
<212> TYPE: DNA
<213> ORGANISM: Artificial Sequence
<220> FEATURE:
<223> OTHER INFORMATION: Primer 2

<400> SEQUENCE: 9
gcaggataac aagtcacact gag                                         23
```

METHODS AND COMPOSITIONS FOR SEGREGATING TARGET NUCLEIC ACID FROM MIXED NUCLEIC ACID SAMPLES

CROSS-REFERENCE TO RELATED APPLICATIONS

This application is a continuation of U.S. application Ser. No. 14/591,291, filed Jan. 7, 2015, which is a continuation of U.S. application Ser. No. 13/958,125, filed Aug. 2, 2013, now U.S. Pat. No. 8,940,296, which is a divisional of U.S. application Ser. No. 13/533,489, filed Jun. 26, 2012, now U.S. Pat. No. 8,927,218, which claims the benefit of the filing date of U.S. Provisional Appl. No. 61/501,569, filed Jun. 27, 2011, each of which are incorporated by reference in their entirety.

STATEMENT REGARDING FEDERALLY SPONSORED RESEARCH OR DEVELOPMENT

This invention was made with government support under Contract Number: HSHQDC-10-C-00019 awarded by the Department of Homeland Security. The government has certain rights in the invention.

REFERENCE TO SEQUENCE LISTING SUBMITTED ELECTRONICALLY

The content of the electronically submitted sequence listing Name: 31790010004_SequenceListing.txt; Size: 2,340 bytes; and Date of Creation: Aug. 11, 2017 is incorporated herein by reference in its entirety.

BACKGROUND OF THE INVENTION

This invention relates generally to methods and compositions for segregating a target nucleic acid from a mixed nucleic aid sample.

Rapid detection and detailed analysis of biological threats is important in mitigating the impact on the target population. The general approach to detection and analysis is gathering an environmental sample (air, water, food, human tissue) and determining whether the sample contains any nucleic acid (DNA or RNA) from the biological threat (bacteria, virus, etc.). The problem primarily encountered in this approach is that the environmental samples are not pure and often contain significantly more background eukaryotic nucleic acid than target biological threat nucleic acid making it difficult to isolate or amplify the target nucleic acid. In fact, complex mixtures of prokaryotic and eukaryotic nucleic acid are the norm in nature; co-mingled communities of organisms exist in air, water and soils, and symbiotic associations of bacteria and plants or humans are a reality of life. Apart from the detection of these biological threats in a sample, there are research and commercial reasons for segregating and isolating the relatively small genomes of biological threats, such as bacteria (4-6 megabases), from larger eukaryotic genomes (2.3 megabases-16 gigabases). In other words, this genome size difference equates to a single human cell providing approximately 1000 times the genetic material to a mixture as a single *Escherichia coli* (*E. coli*) cell. This has the effect of generating an overwhelming amount of eukaryotic DNA from most mixed samples creating an impediment to the detection and identification of bacteria in a mixed sample.

Sepsis is one example of a situation where detection of a biological threat is very difficult. Sepsis is the leading cause of death in non-coronary intensive care units worldwide and its complex range of etiological agents include gram-positive and gram-negative bacteria. Levels of bacteria in the blood have been reported to be in excess of 1000 colony forming units (CFU) per mL of blood and in other cases at less than 1 CFU per mL of blood. Even at the most concentrated levels, approximately 1000 bacteria per ml of blood, the bacterial DNA would be overwhelmed by $10^9$ blood cells ($10^7$ contain DNA) in the same volume which equates to ten-million fold more human DNA than bacterial DNA.

A comprehensive solution to separation and isolation of bacterial DNA from a mixed sample containing eukaryotic DNA is currently unavailable. Mixed samples are often cultured to differentially amplify the percentage of bacteria in a sample. Indeed, for sepsis, the standard of pathogen identification in reference labs remains detection via cultures. Typically, cultures require 1 to 5 days for the pathogen to grow out sufficiently for confirmation. Culture methods are also the standard for food testing and environmental samples. Identification of bacterial infections has become more rapid in anthrax infections by monitoring for plaques made by *B. anthracis*-specific phage providing greater than 90% sensitivity and specificity. However, FDA approved phage lysis assays are laboratory based, require 8-24 hours for completion by skilled technicians and only enumerate the bacteria rather than purify it out for analysis.

In an alternative to culture-based detection methods, nucleic acid isolated from mixed prokaryotic/eukaryotic environmental samples can be subjected to highly sensitive polymerase chain reaction (PCR)-based assays to detect biological threat target sequences. For example, the FDA has approved a rapid real-time PCR technology for the identification of specific threats such as *S. aureus* and *Streptococcus* spp. from nasal swabs. The *S. aureus* Gene Ohm kit (Becton Dickinson, USA) requires suspension of a nasal swab, rapid lysis followed by amplification in approximately 2 hours with a published sensitivity of 98.9% and specificity of 96.7%. However, the eukaryotic nucleic acid background of a nasal swab sample is low compared to a blood sample. Moreover, this method is limited to pure detection of a specific bacteria and thus, does not permit isolation and purification of the bacterial target genome for analysis and would not be effective in detecting unknown prokaryotic threats.

Detection of bacteria in blood has been achieved from crude lysates generated via mechanical/chemical lysis. In this approach, detection of the prokaryotic DNA requires expensive, real-time PCR assays, such as the Roche Septi-Fast™ system, or alternatively, mass spectrometry assays such as the Abbot Plex-ID system. These systems are not FDA approved and can only handle 1.5 ml of blood limiting its sensitivity. Moreover, these assays also do not permit isolation and purification of genetic material from the prokaryotic threat for additional analysis.

Thus, a method is needed that allows for selective isolation of the prokaryotic nucleic acid in a mixed sample thereby permitting further analysis and characterization of the target prokaryotic genome. Furthermore, a method is needed that permits separation and isolation based on non-specific prokaryotic traits such that identification and characterization of previously unknown bacterial threats is possible. Finally, a method is needed that does not require expensive quantitative PCR assays.

BRIEF SUMMARY OF THE INVENTION

In view of the problems associated with current isolation protocols, the present invention provides methods, compositions and kits for efficient segregation of a nucleic acid from a mixed sample of nucleic acid (e.g., prokaryotic or bacterial nucleic acid from a eukaryotic nucleic acid). In some embodiments, the process exploits epigenetic modifications of DNA that are unique to prokaryotic kingdoms thereby providing a rapid and efficient isolation and identification of prokaryotic nucleic acid from a mixed environmental or clinical sample. As such, the invention permits rapid diagnosis and allow for further genomic characterization and analysis of biological threats.

In one embodiment, the method involves the steps of: (1) applying an epigenetic binder to a sample under conditions sufficient to permit the epigenetic binder to form a complex with nucleic acid carrying the epigenetic modification; (2) isolating the epigenetic binder/nucleic acid complex; (3) purifying the nucleic acid present in the isolated complex; and (4) analyzing the purified nucleic acid. In one aspect, the epigenetic binder is a molecule or molecular complex that specifically binds prokaryotic epigenetic modifications such as those selected from the group consisting of N4-methylcytosine (N4mC), N6-Methyladenine (N6 mA), and any other prokaryotic-specific epigenetic modifications. The epigenetic binder is selected from the group consisting of polyclonal antibodies, monoclonal antibodies, conjugated polyclonal or monoclonal antibodies, restriction enzymes, conjugated restriction enzymes, binding-mutant restriction enzymes, and other molecules or molecular complexes having specific affinity to the aforementioned epigenetic modifications.

In another embodiment, an epigenetic-specific digestion method is provided. The method includes applying an epigenetic-specific digestion factor to a sample under conditions sufficient to permit the factor to selectively cleave nucleic acid at a subsequence that is void of a particular epigenetic modification, wherein the epigenetic modification is present in the target nucleic acid. Following the epigenetic-specific cleavage, the non-target nucleic acid is depleted and the target nucleic acid is analyzed. Additional steps can be added to this method which will be discussed further in the detailed description below.

In another embodiment, an epigenetic-binder composition is provided. In a preferred embodiment, the epigenetic binder is a monoclonal antibody or antigen binding fragment thereof directed to an epigenetic modification specific to the target nucleic acid, such as N4mC or N6 mA. In a related embodiment, the epigenetic binder is a mutated restriction enzyme that selectively binds, but does not cleave the target nucleic acid at a subsequence carrying an epigenetic modification specific to the target nucleic acid. In either embodiment, the epigenetic binder is optionally biotinylated or conjugated with a second molecule to aid in isolation of the binder/nucleic acid complex from the sample.

The present invention is not limited to the embodiments set forth above and other embodiments and applications will become apparent from the discussion and examples provided in the detailed description below.

BRIEF DESCRIPTION OF THE DRAWINGS

The various embodiments of the invention can be more fully understood from the following detailed description and figures, which form a part of this application.

FIG. 1A shows the sequence of a synthetic adaptor used for MADA demonstrations (SEQ ID NO:1). The adaptor has polynucleotide overhangs compatible with GATC sites. Primers enable amplification of fragments containing the adaptor (e.g., Primer #1 and Primer #2 as indicated)(SEQ ID NOs:8 and 9). A NotI restriction site is present for linearization of fragments as needed. FIG. 1B shows alternative synthetic adaptor sequences that can be used for MADA demonstrations (SEQ ID NOs:2-7, wherein SEQ ID NOs: 2 and 3 anneal, SEQ ID NOs: 4 and 5 anneal and SEQ ID NOs: 6 and 7 anneal).

Figure 3:
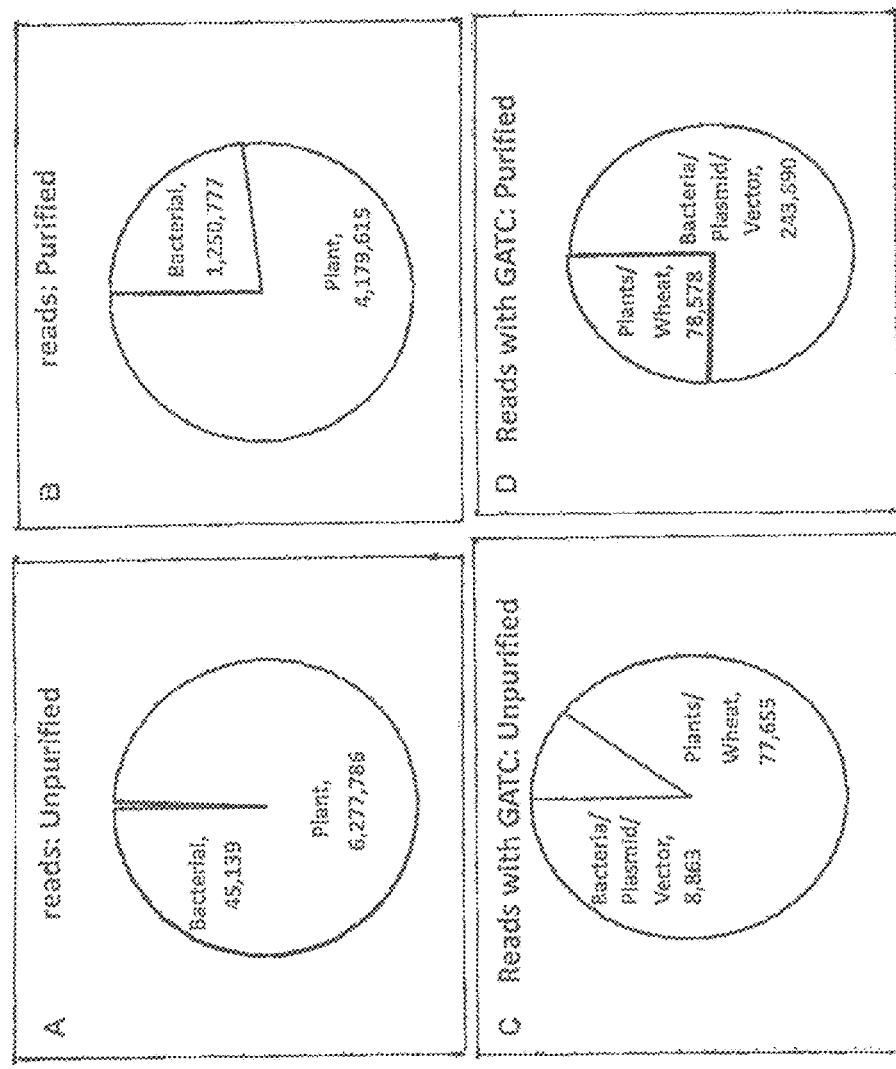

Ultrahigh-Throughput Screening (UHTS) identification of mappable sequence reads shows enrichment of bacteria in FIG. 3. MegaBlast categorization of sequences is plotted showing a nearly 30× enrichment in bacterial sequences (3A and 3B). Analysis of sequence reads containing a GATC site in the digested organism mixture, pre- and post-purification are also shown (3C and 3D).

Figure 4:
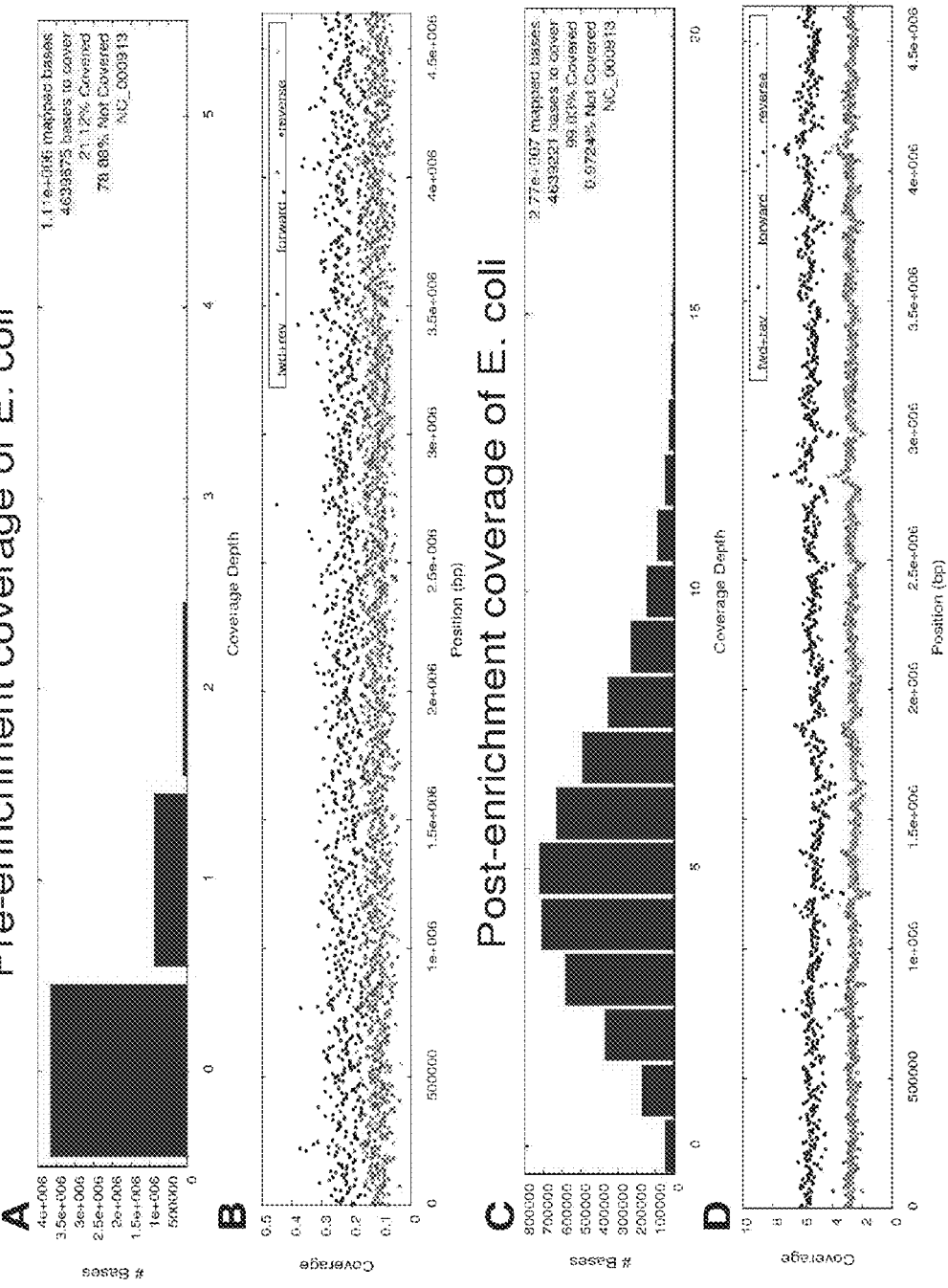

FIG. 4 shows N6 mA enrichment leads to high uniform coverage of *E. coli* K-12 MG1655. The ICx Bioassays SPEED pipeline was used to map the first 32 bp of each read to a linear representation of the chromosome. (4A and 4C). Coverage depth jumped from 0.24 prior to enrichment to 6.0× following enrichment. The resulting coverage level of 99% is listed. (4B and 4D). Coverage by position reveals even distribution across the chromosome.

Figure 5:
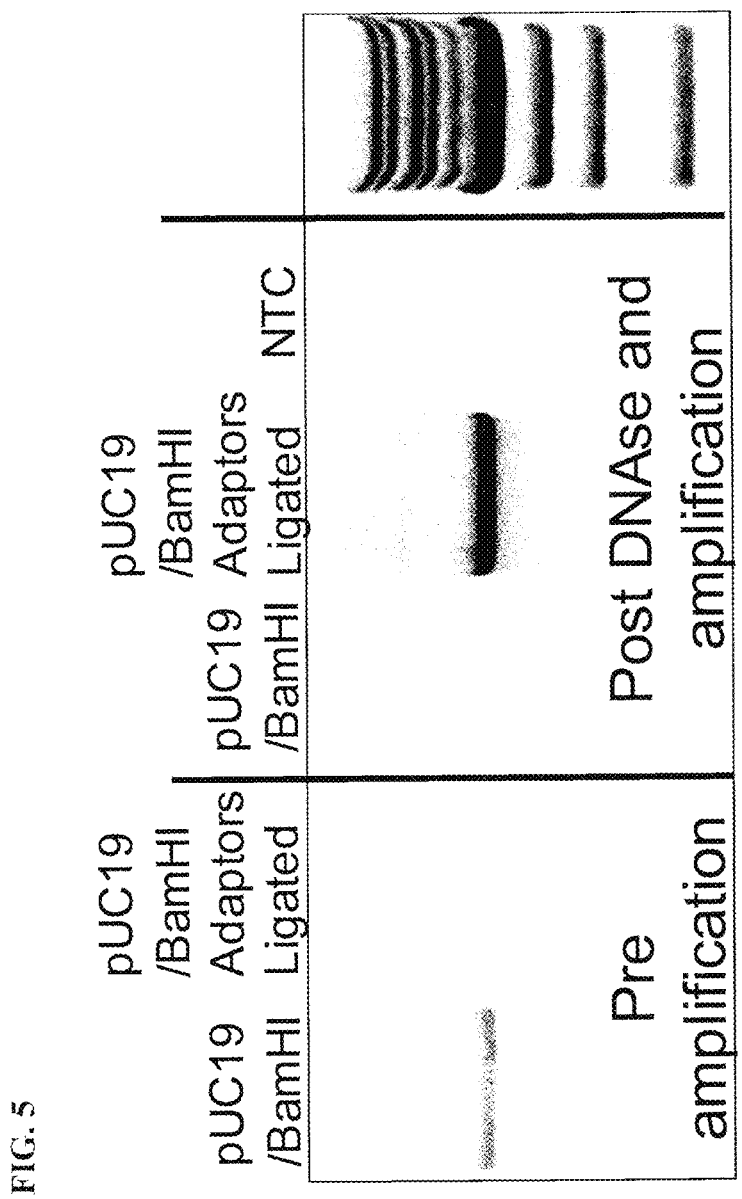

FIG. 5 shows adaptors ligated to sticky BamHI ends circularizes molecules and protects them from digestion enabling PCR amplification. A 1.0% TAE agarose gel was run with the following samples: Lane 1; 100 ng of plasmid pUC19 was digested with BamHI. Lane 2; 100 ng of pUC19 after the addition of BamHI-adaptors. The samples from lane 1 and 2 were subsequently treated with plasmid-safe exonuclease and subjected to PCR amplification using primers specific to the BamHI-adaptors. Lane 3; BamHI digested pUC19 after DNase and amplification treatment. Lane 4; pUC19 with ligated BamHI-adaptors after DNase and amplification treatment. Lane 5; No template control (NTC) that underwent BamHI-adaptor ligation, DNAse, and amplification treatment. Lane 6; molecular weight marker.

Figure 6:
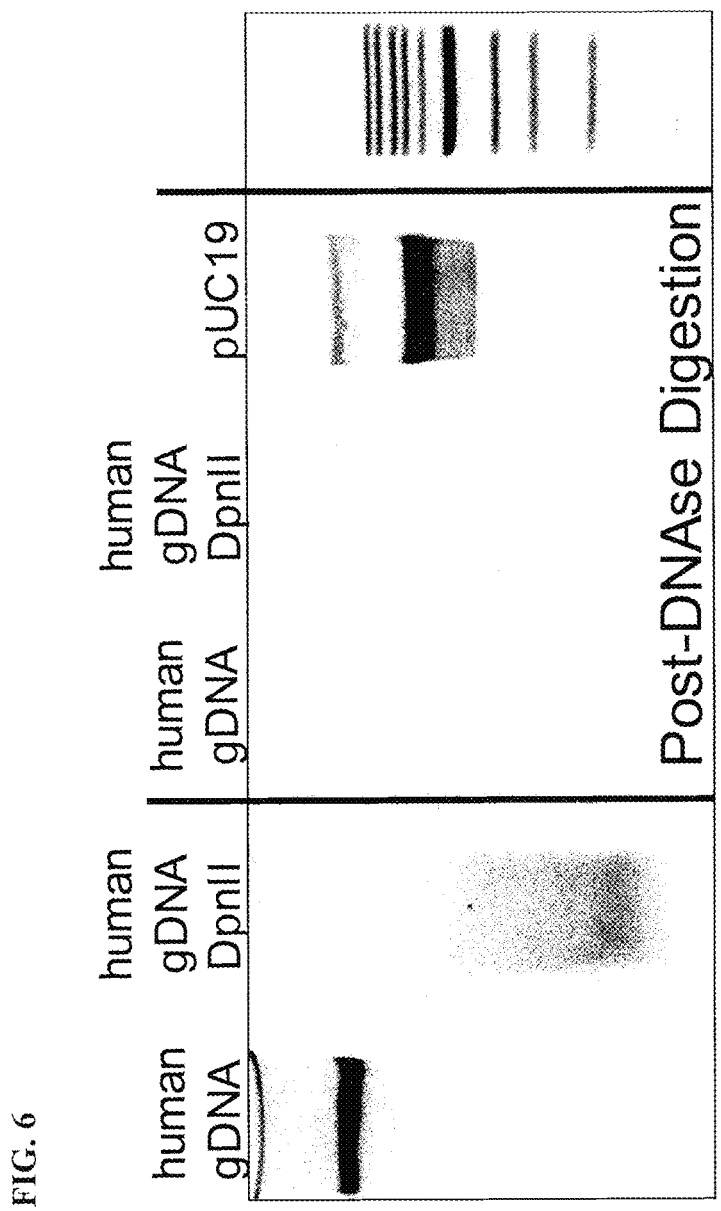

FIG. 6 demonstrates selective digestion of linear versus circular DNA molecules which enables selective amplification of target molecules. The 1.0% TAE agarose gel left hand panel shows the input human genomic DNA before (lane 1) and after (lane 2) DpnII digestion. The middle panel shows the results post plasmid safe DNAse digestion on human genomic DNA (lane 3), human genomic DNA cut with DpnII (lane 4) and on pUC19 (lane 5). DpnII restricted human genomic DNA (gDNA) is sensitive to plasmid safe DNAse (compare lanes 2 and 3), whereas circular molecules generated by adaptor ligation (lane 5, pUC19 control) are not.

Figure 7:
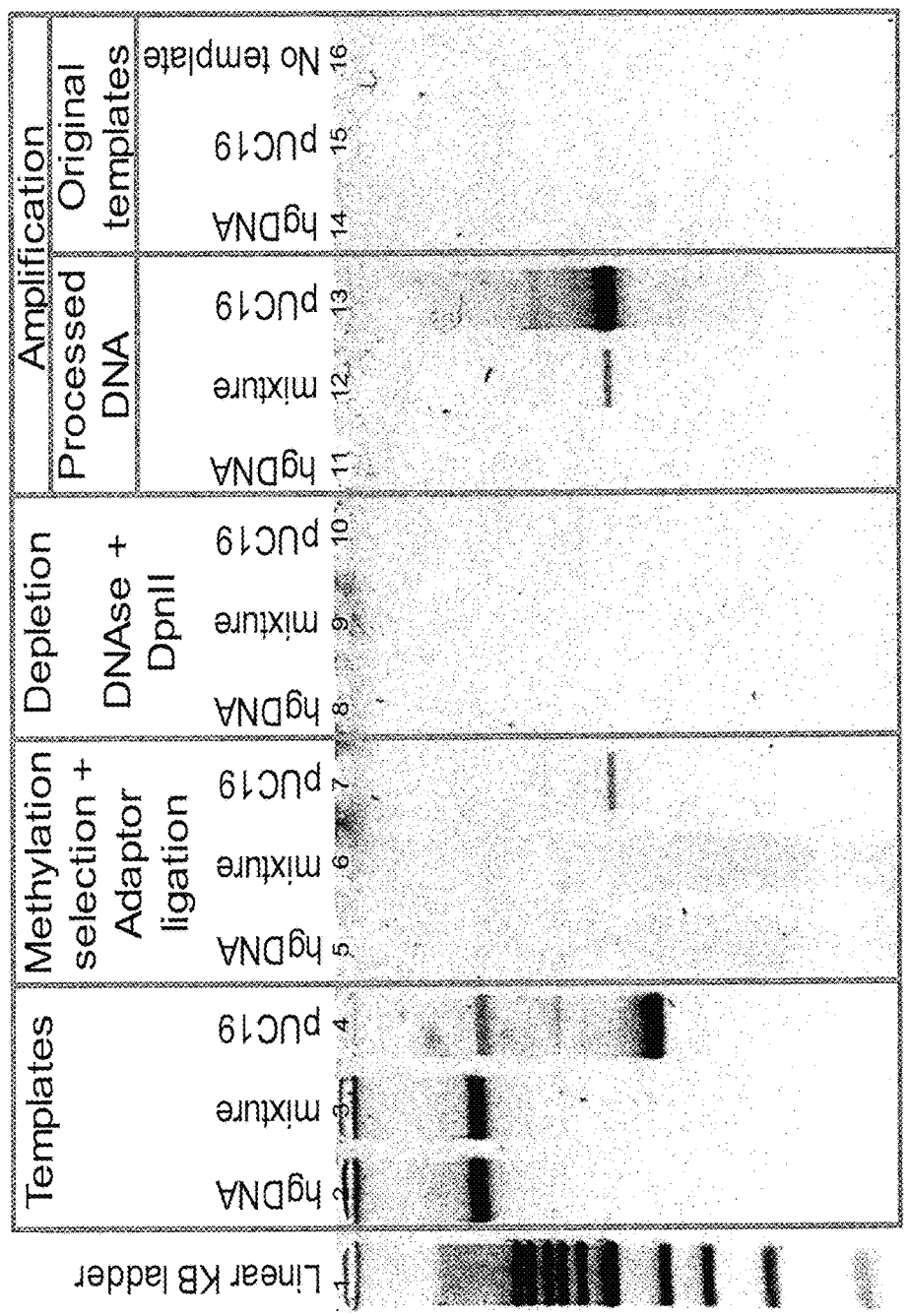

FIG. 7 demonstrates that the epigenetic-specific digestion method with adaptor ligation is effective to isolate and amplify target DNA in a mixed sample. A linear KB molecular weight ladder is in lane 1. Templates include Lane 2: human genomic DNA (hgDNA), Lane 3: mixture containing 1 ng of pUC19 DNA (GATC methylated bacterial DNA) and 1 ug of human genomic DNA, and Lane 4: supercoiled pUC19. Methyl-selection and adaptor ligation on these same templates is shown in lanes 5-7. Templates were digested by DpnII, blunted with T4 polymerase a subsequent BamHI digestion, column purification and adaptor ligation mediated circularization. Note the smear of human DNA and preservation of bacterial DNA. The third panel demonstrates Depletion and DNAse+DpnI treatment of the templates. Depletion of human DNA was achieved by Plasmid Safe DNAse and DpnII digestion (Lanes 8-9). The last panels show Amplification of templates that were Processed or the Original templates. PCR with adaptor specific primers amplifies pUC19 (Lane 13) even from the digested mixture (Lane 12) but not from human only DNA (Lane 11). Template negative controls of unprocessed hgDNA (Lane 14), unprocessed pUC19 (Lane 15) or no template do not generate an amplified signal.

Figure 8:
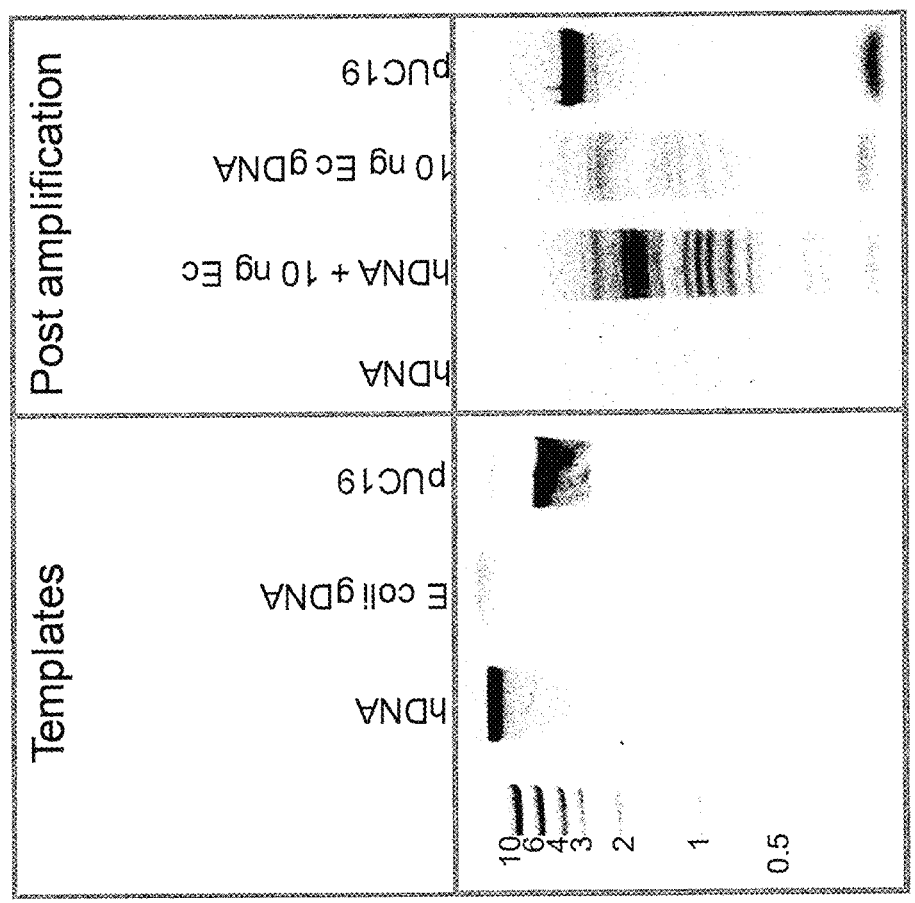

FIG. 8 demonstrates that the epigenetic-specific digestion method with adaptor ligation effectively amplifies bacterial genomic DNA while selectively degrading human genomic DNA in a single mixture. A 1.0% TAE agarose gel was run with samples as listed. Linear KB molecular weight ladder (lane 1). The left panel of the gel includes Templates; human genomic DNA (hDNA, Lane 2), E. coli genomic DNA (gDNA, lane 3), and Supercoiled pUC19 (lane 4). The right panel of the gel includes the same templates Post Amplification (including methyl-selection and adaptor ligation, Depletion+DNAse and amplification); human genomic DNA (hDNA, Lane 5), mixture of 10 ng of E. coli gDNA and 1 ug of human genomic DNA; 10 ng of E. coli genomic DNA (Ec gDNA, lane 6); and Supercoiled pUC19 (lane 7).

Figure 9:
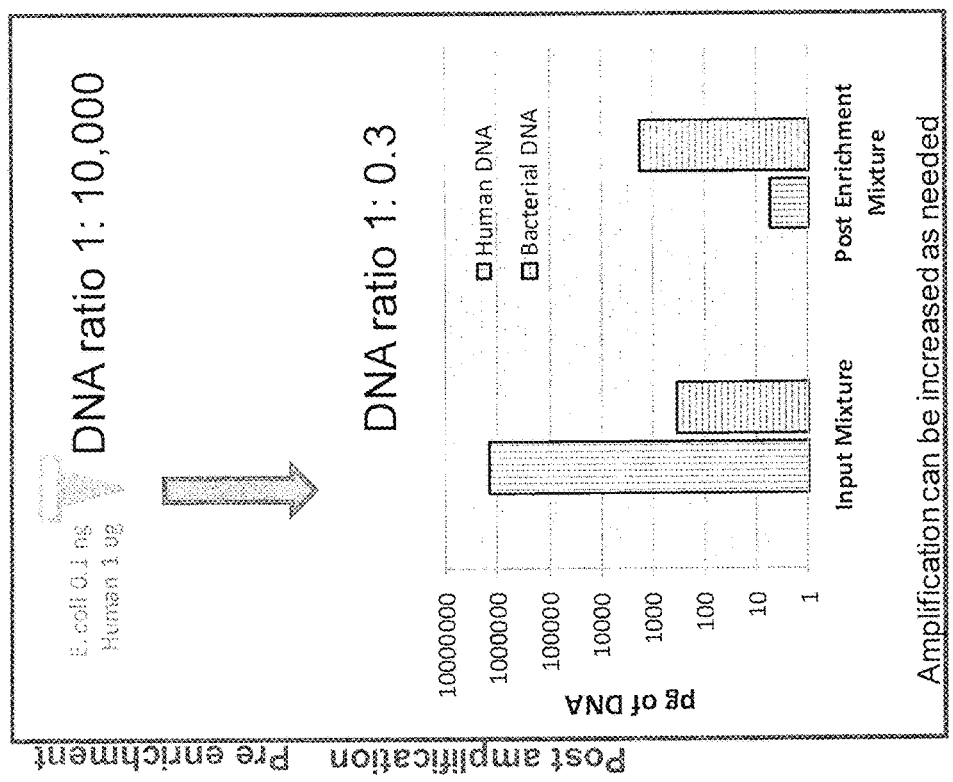

FIG. 9. quantifies the level of bacterial genome enrichment and human genome degradation using QPCR after epigenetic specific enrichment. Primers and probes to the DYZ locus of human male DNA and the 16S locus of E. coli bacterial DNA were used to measure the levels of genomic DNA from each organism in the mixture before and after amplification. A Pre-enrichment sample of 0.1 ng E. coli genomic DNA was mixed with 1 ug human DNA (1:10,000) to generate the qPCR measurements of the Input Mixture. The post Enrichment qPCR measurement depicts a resulting ratio of 1:0.3.

Figure 10:
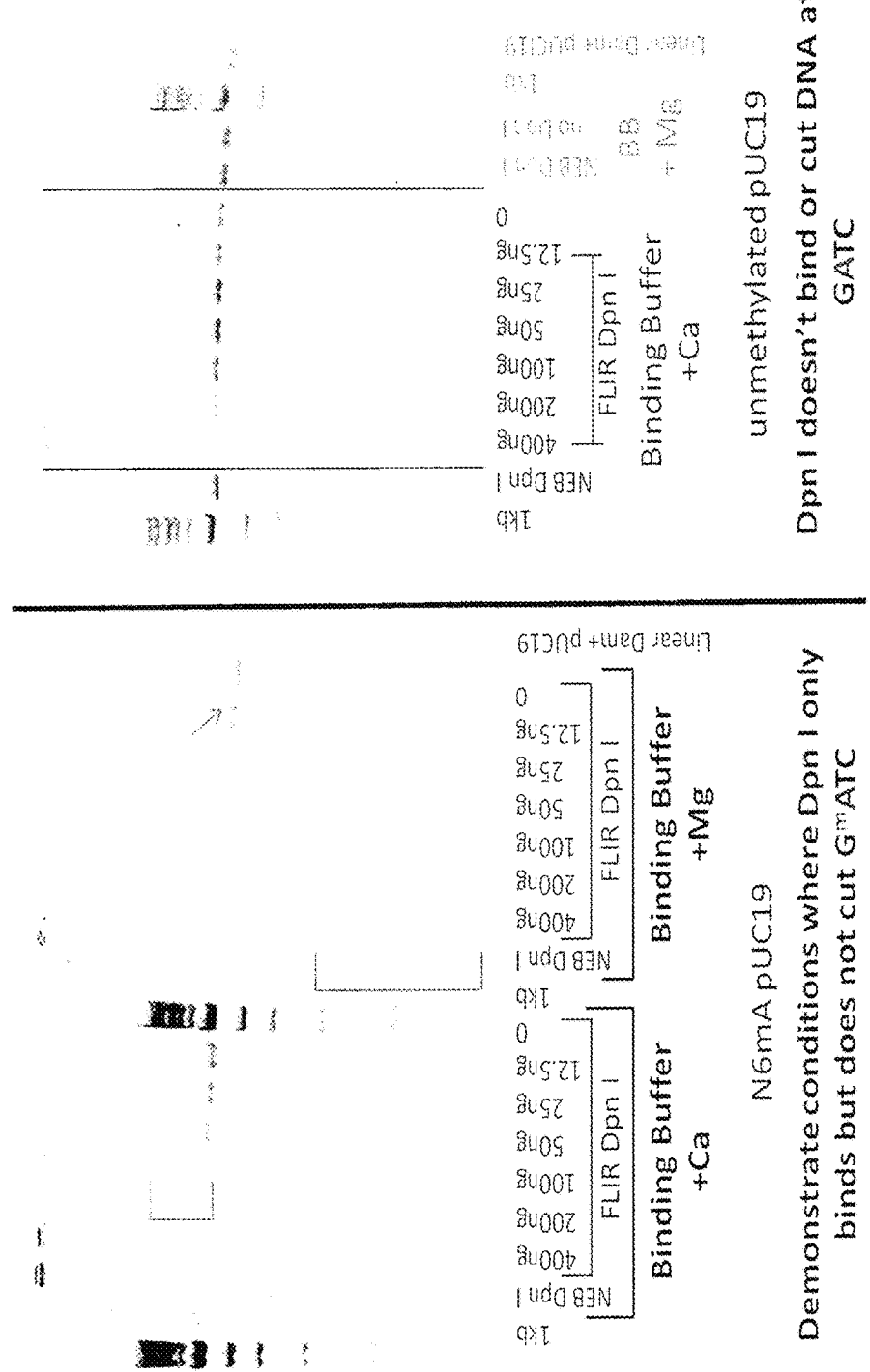

FIG. 10 demonstrates that under modified conditions, restriction enzymes can selectively bind N6 mA without cutting. A 2% agarose gel was used to separate DpnI-DNA complexes from unbound DNA by electrophoresis at 100 V for one hour at room temperature. The gels were imaged using an Alpha Imager HP from Cell Biosciences. The left gel used only pUC19 DNA methylated at GATC sites by passage in the dam+ strain, MG1655. pUC19 was linearized in lane 19. A titration of 400 ng to 0 ng of FLIR produced DpnI was incubated with the methylated template in 15 ul for two hours at 37° C. with Ca++(lanes 3-9) or with Mg++(lanes 12-18). The same binding conditions were used for NEB produced DpnI with Ca++(lane 2) or with Mg++ (lane 11). Lanes 1 and 10; 1 KB molecular weight marker. The right panel gel used only unmethylated pUC19 via passage in the dam-strain, BL21. Unmethylated pUC19 for was incubated with FLIR produced DpnI in a titration of 400 ng to 0 ng in 15 ul for two hours at 37° C. with Ca++(in lanes 3-9). or with Mg++(lanes 12-18). The same binding conditions were used for NEB produced DpnI with Ca++(lane 2) or with Mg++(lane 11). Lanes 1 and 12; 1 KB molecular weight marker. pUC19 was linearized in lane 19.

Figure 11:
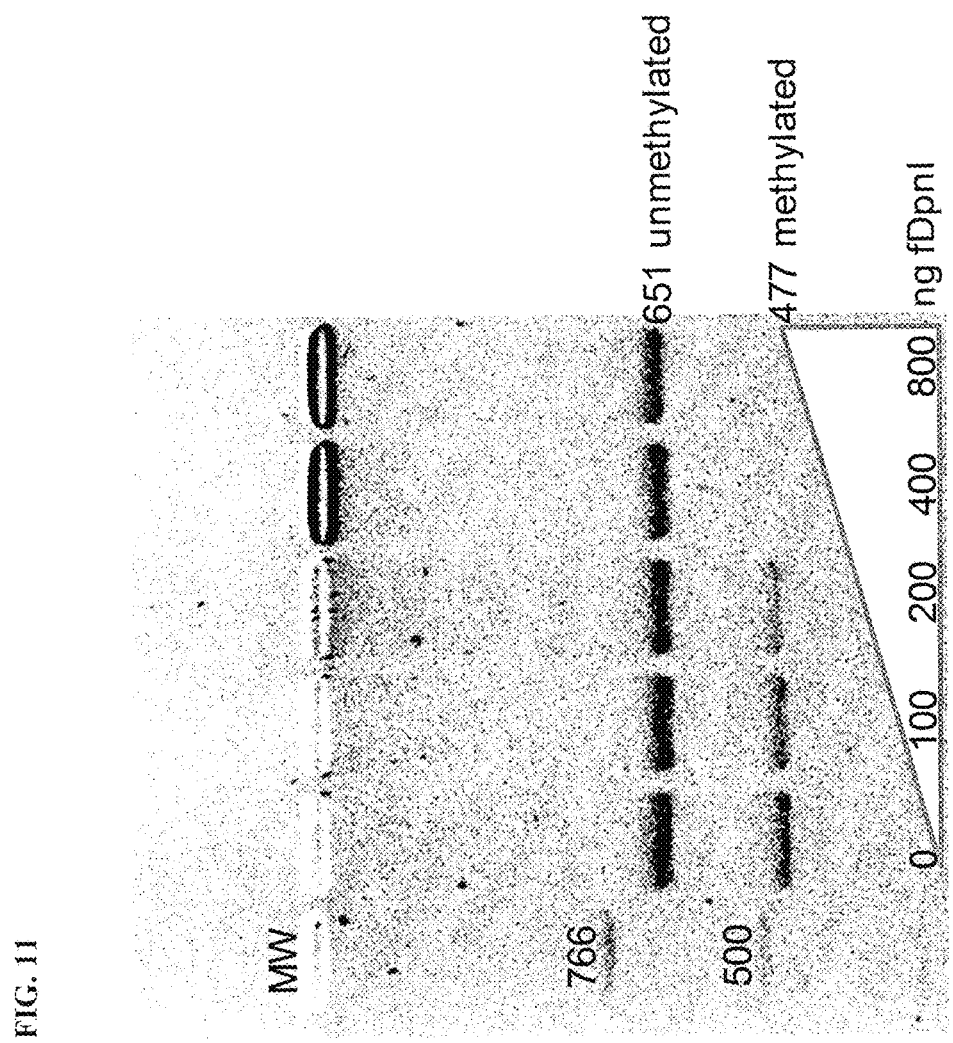

FIG. 11 demonstrates that biotinylated DpnI (bDpnI) specifically binds and retards gel migration of a methylated 477 bp DNA fragment in preference to an overlapping unmethylated 651 bp DNA fragment.

Figure 12:
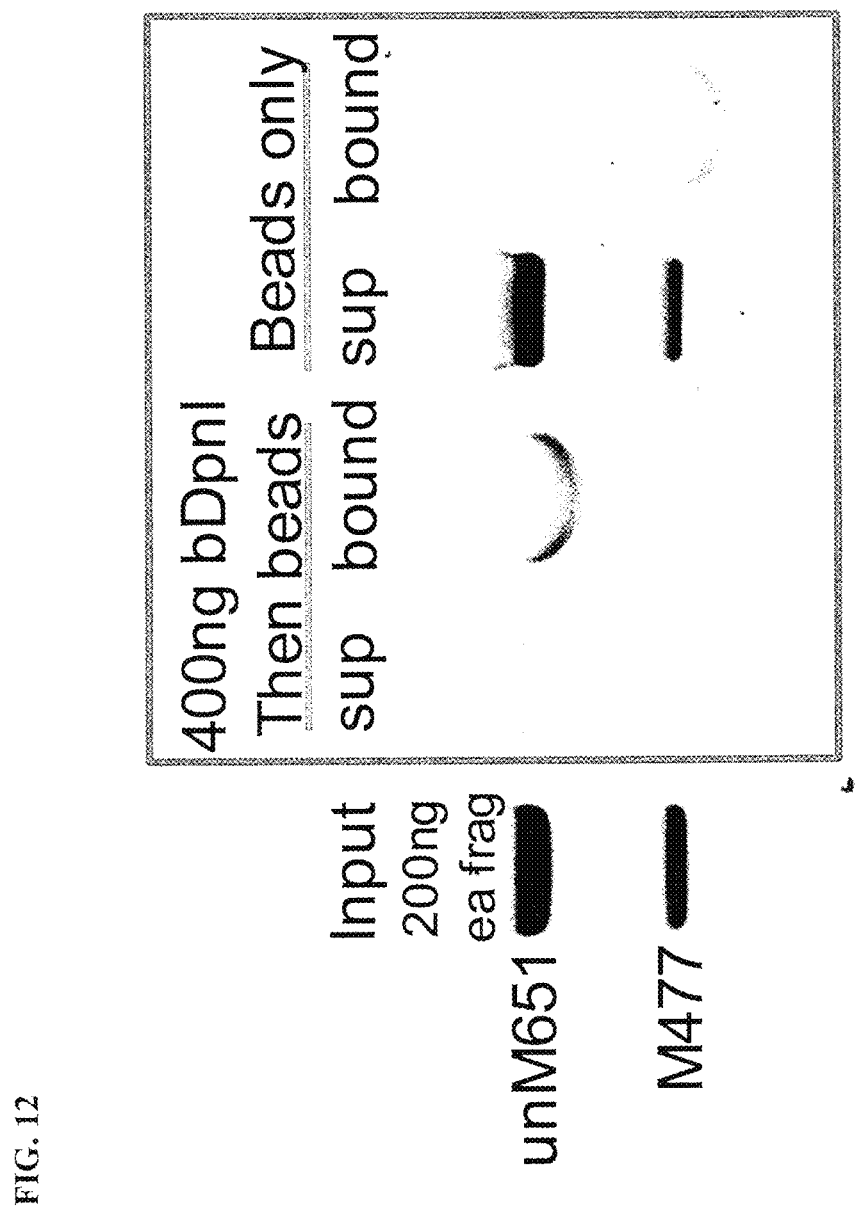

FIG. 12 demonstrates bDpnI incubated first with methylated 477 bp DNA fragments and then with avidin beads shows lower specificity than when avidin beads are pre-coated with bDpnI.

Figure 13:

FIG. 13 demonstrates the specificity of target DNA binding on sentinel DNA fragments assessed by gel analysis. A nontarget DNA fragment (651 bp) was PCR amplified from pUC19 and a target DNA fragment (477 bp and internal to the nontarget product) was PR amplified then treated with dam methyltransferase to confer the Gm6ATC modification. After gel purification, 100 mg of each fragment was mixed and bound with 80 ul to 180 ul of biotinylated-DpnI coated avidin beads. After thirty minutes, samples from input mixture (far left lane 1), the bead wash (middle panel lanes 2-5) or the bead eluted fractions (right panel, lanes 6-9) were loaded onto a 3% agarose gel. Sentinel fragments can be used as a control to evaluate the efficiency of a reaction.

Figure 14:
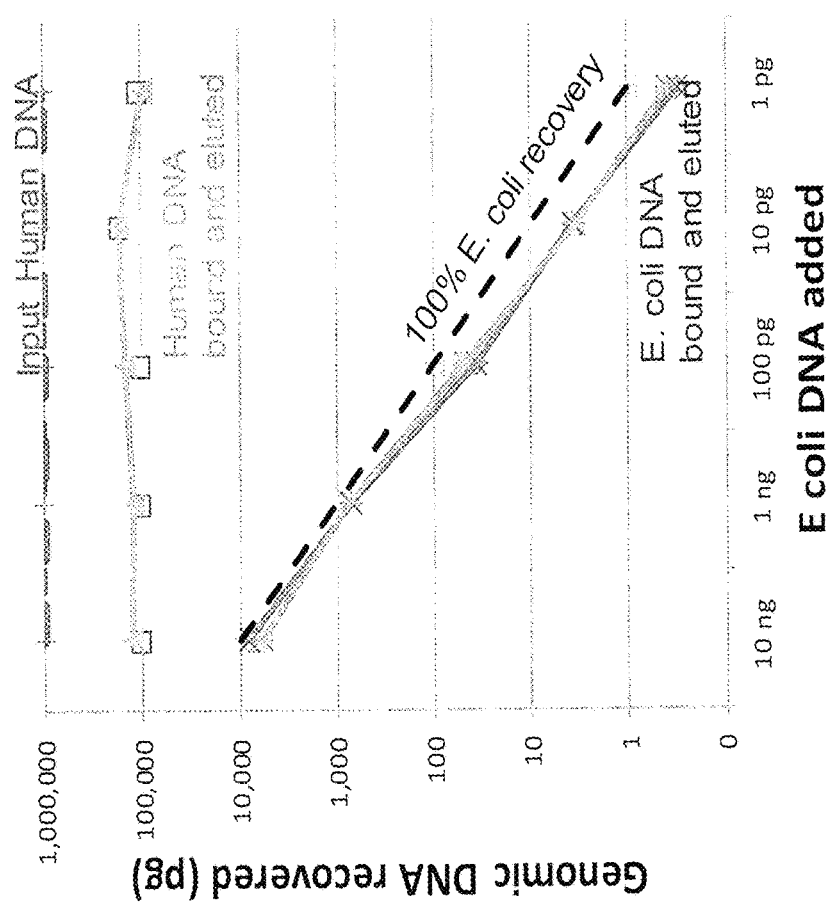

FIG. 14 demonstrates the efficiency of bacterial target DNA recovery from a mixed sample containing 1 ug of human DNA. Decreasing amounts of E. coli genomic DNA (10 ng-1 pg) were spiked into 1 ug of human DNA. Recovery was assessed with quantitative polymerase chain reaction (qPCR) to bacterial 16S and human DYZ, each normalized to their respective marker frequency.

Figure 15:
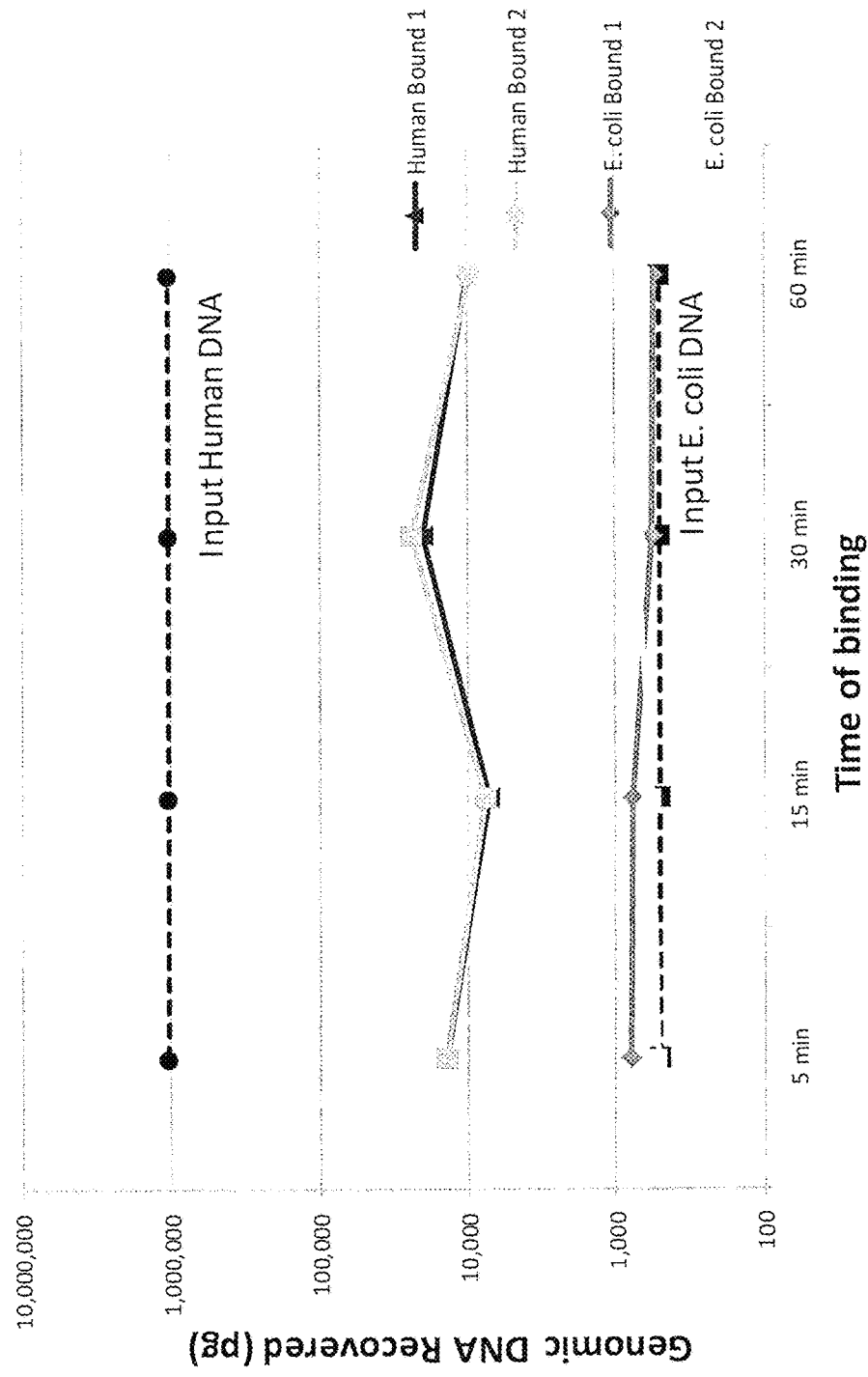

FIG. 15 shows a binding time course of bacterial and human DNA that demonstrates rapid binding and high specificity of embodiments of the invention. bDpnI coated beads were added to a mixture of 500 pg of E. coli (dashed line with squares) and 1 ug of human male DNA (dashed line with circles). At the times indicated, the beads were collected with a magnet and washed. qPCR for the 16S gene of E. coli or DYZ of human was used to quantify the amounts bound.

FIG. 16 shows an exemplary genomic mixture and the effect of SCODA and the DpnI enrichment process.

FIG. 17 demonstrates that DpnI enrichment increased genome coverage approximately 15 fold without introducing significant biases across the 4.6 MB genome. 17A shows pre-enrichment coverage with an insert showing the same data on a 20× increased scale to highlight the genomic coverage pattern pre-enrichment. 17B shows post-enrichment coverage is dramatically increased. Key features such as the low and high points of genomic coverage (Terminus and Origin of replication (OriC), respectively), and artificial spikes in coverage (bacteriophage DLP, Rec, and Qin) are indicated.

Figure 18:
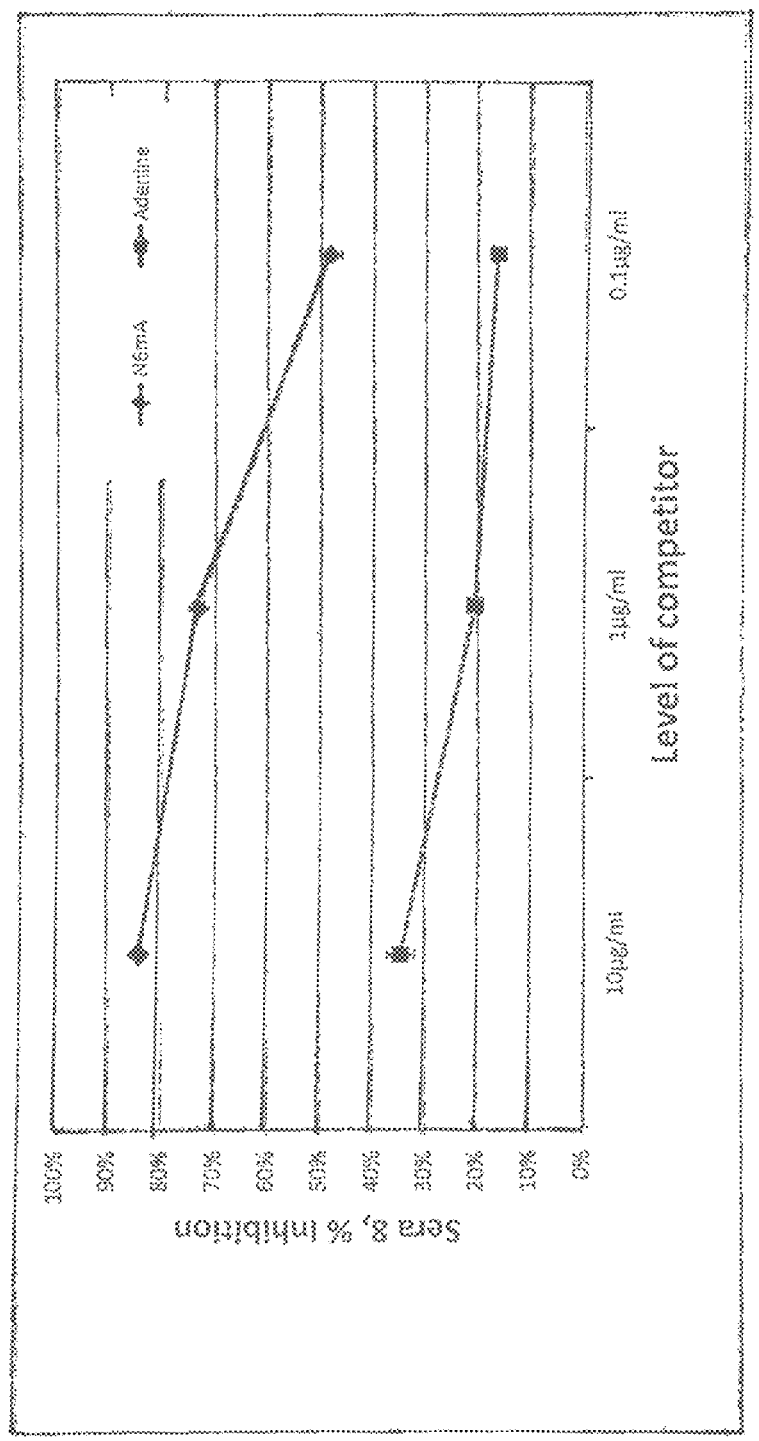

FIG. 18 shows the specificity of antisera to N6-Methyl-2-deoxyadenosine (N6 mA). Triplicate sera samples were tested in a competitive ELISA format by challenging with various levels of Adenine (square) or N6 mA (diamond). Error bars depict the standard deviation among the samples. Only 100 ng of N6 mA results in 50% inhibition of sera binding to N6 mA coated ELISA plates. For comparison, 10 ug of Adenine (a 100 fold increase in reagent) resulted in about 30% inhibition.

Figure 19:
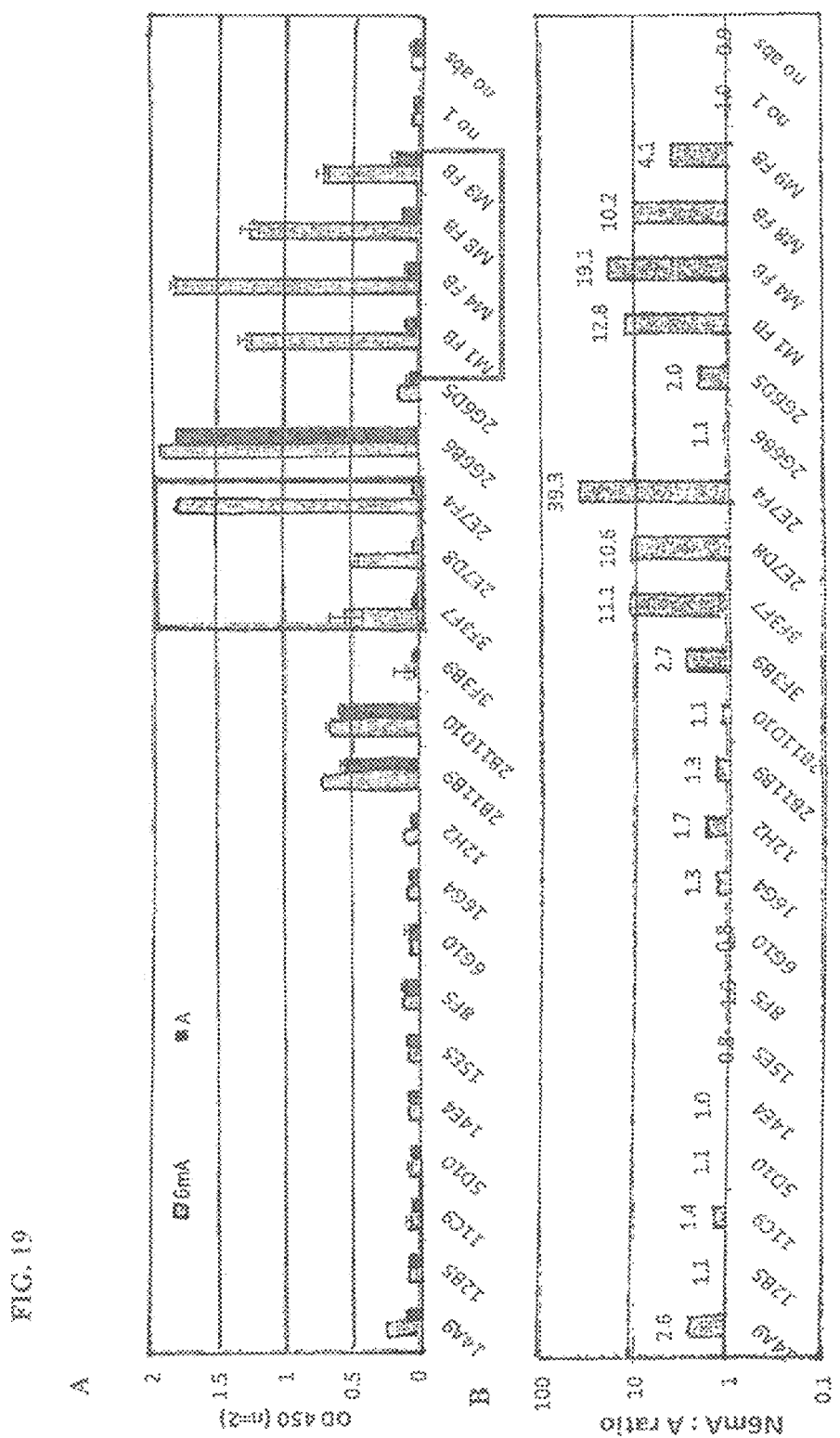

FIG. 19 shows the ELISA signal from tested polyclonal and monoclonal antibodies on methylated and unmethylated oligonucleotides. 19A shows oligonucleotides containing Adenine (A) or N6m-Adenine (6 mA or N6 mA) were immobilized in microliter wells and tested for their binding to various antibodies. High signal from N6 mA oligos and correspondingly low signal from unmethylated oligos is indicative of specificity as exemplified by the three boxed off clones. These can be compared to the final bleed polyclonal sera from mice 1, 4, 8, 9 (four boxed off clones). A no antibody control is also shown (no abs). 19B shows the signal ratio of 6 mA to A.

Figure 20:
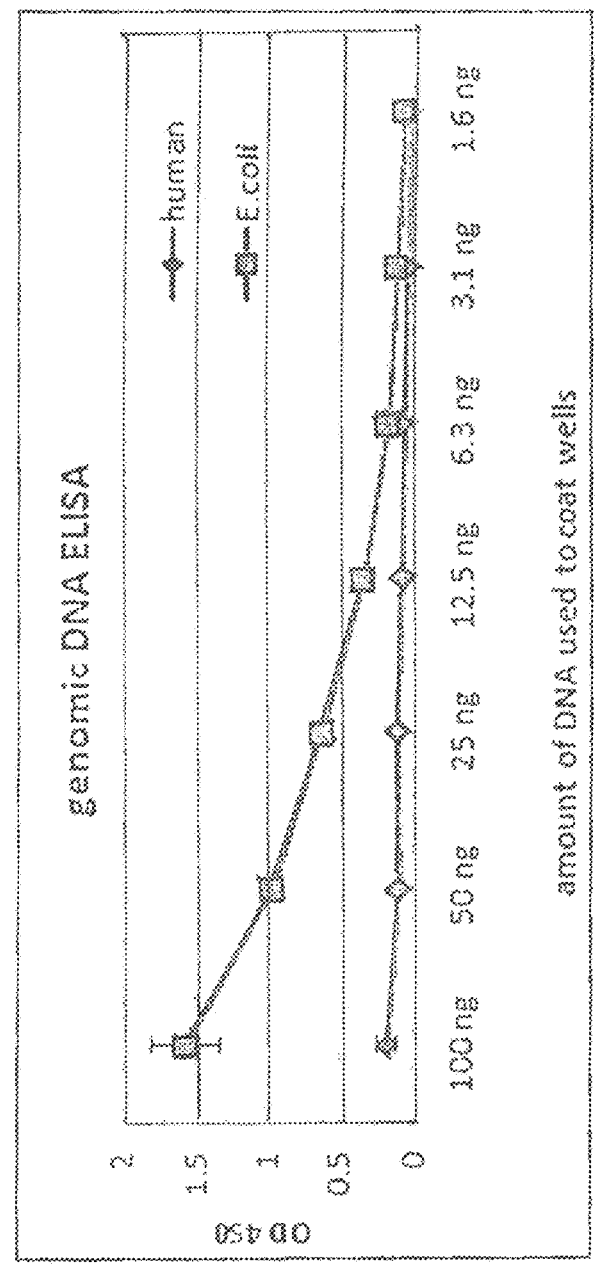

FIG. 20 shows the specificity of the antibodies of FIG. 19 to human and *E. coli* genomic DNA. An ELISA was run using a titration of listed genomic DNA in each well. The optical density at 450 mm (OD450) shows the reactivity of the antibody to each genome.

Figure 21:
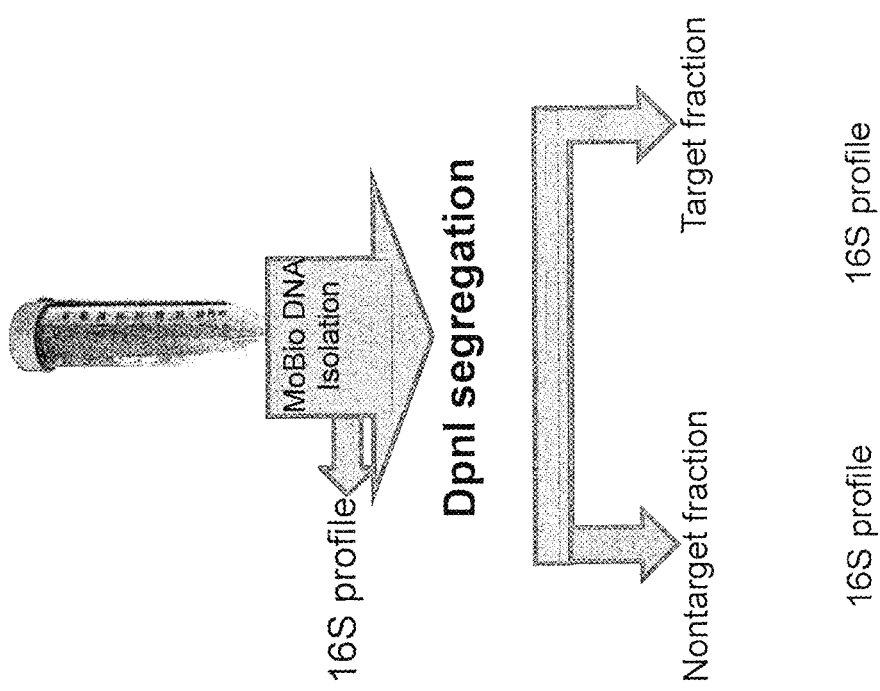

FIG. 21 shows a process flow chart for the methods of Example 7.

Figure 22:
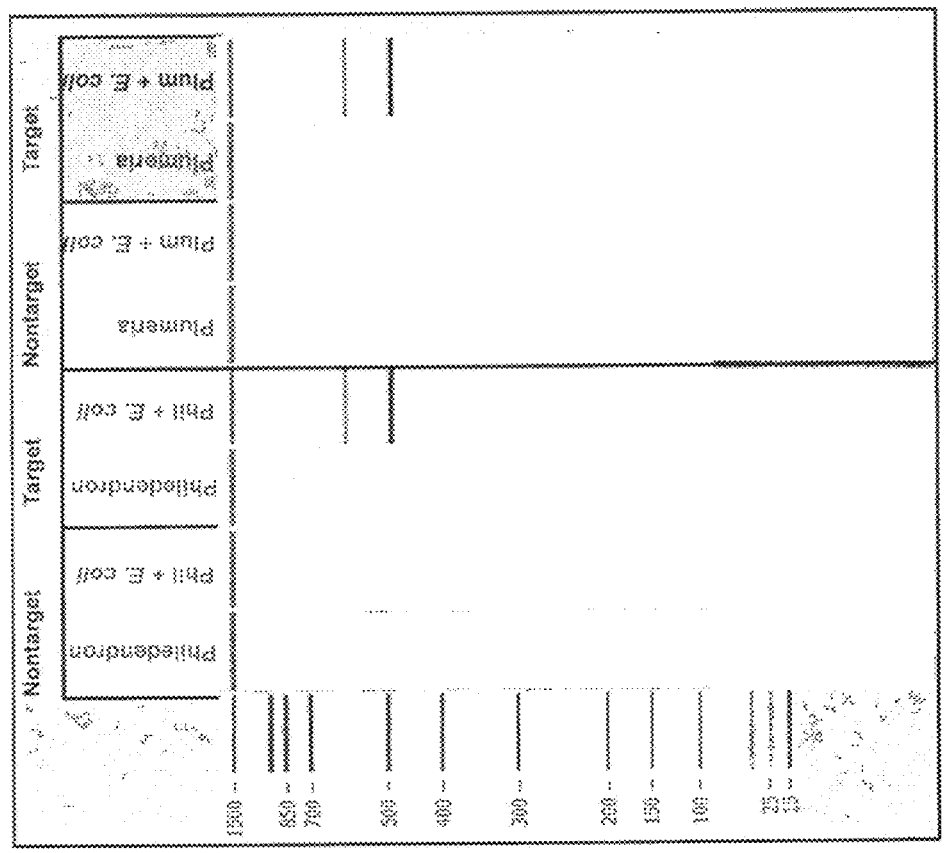

FIG. 22 demonstrates that *E. coli* DNA spiked into soil samples failed to amplify in comparison to *E. coli* DNA alone, implicating that inhibitor of PCR are present in soil samples. Commercial top soil samples high in humic acids were collected from under a philodendron or *plumeria* plant. DNA was extracted from all soil samples using the MoBio Power Soil kit. DNA was subsequently enriched using DpnI coated beads. DNA from the philodendron soil generated a DpnI wash fraction (Nontarget in the left panel) and a DpnI bound and eluted fraction (Target in the left panel). Additionally, 50 ng of *E. coli* DNA was spiked into each fraction (+*E. coli*) to test PCR inhibition of each fraction. The right panel contains Nontarget and Target fractions of the *plumeria* soil DNA + or − *E. coli* DNA spikes. This process is further detailed in Example 8.

Figure 23:
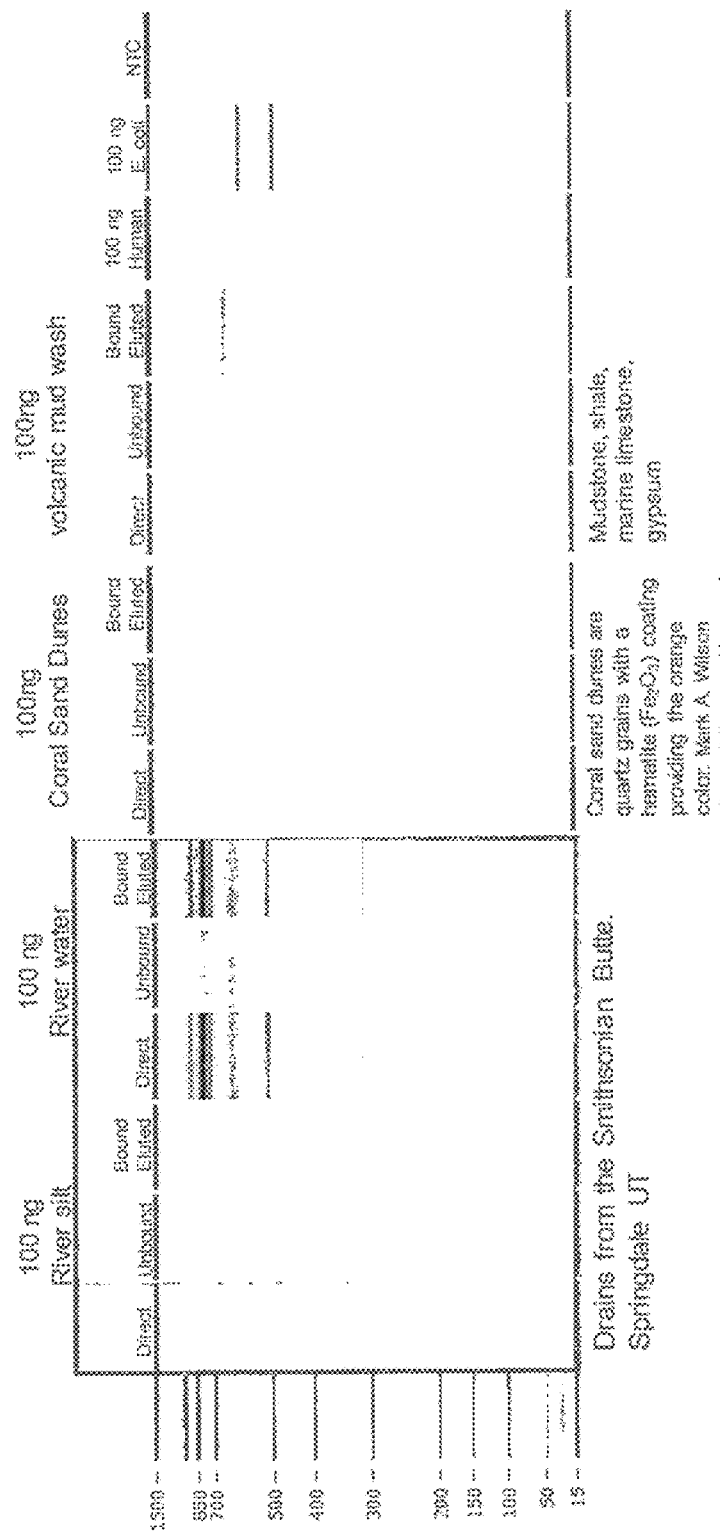

FIG. 23 shows 16S PCR profiling of DNA isolated from river bed silt or surface river water, hematite coated sand, or volcanic mud. The MoBio Power Water kit was used to isolate DNA from 200 mls of river water, and the MoBio Power Soil kit was used to isolate DNA from 250 ng of River silt, the Coral Sand Dunes and the Volcanic mudwash samples. 100 ng of each sample was used directly for 16S PCR amplification (direct samples are in Lanes 2, 5, 8, 11). Another 100 ng of DNA from each sample was then used for extraction with DpnI coated magnetic beads to generate the bound eluted fraction and an unbound fraction. Lane 1 is a molecular weight marker. Other lanes include River silt 16S PCR fractions (Lanes 2-4), River water 16S PCR fractions (lanes 5-7), Coral San Dune 16S PCR (lanes 8-10) and Volcanic mud wash samples (lanes 11-13). A No Template Control (NTC, lane 14) and 100 mg of human DNA (lane 15) did not amplify with 16S primers, while 100 ng of *E. coli* DNA (lane 16) produced bands characteristic of a bacterial organism. In addition, isolated DNA and unbound fractions from riverbed silt, Coral Sand Dunes, and Volcanic Mud Wash did not amplify. The Bound and Eluted fraction amplified from all samples.

Figure 24:
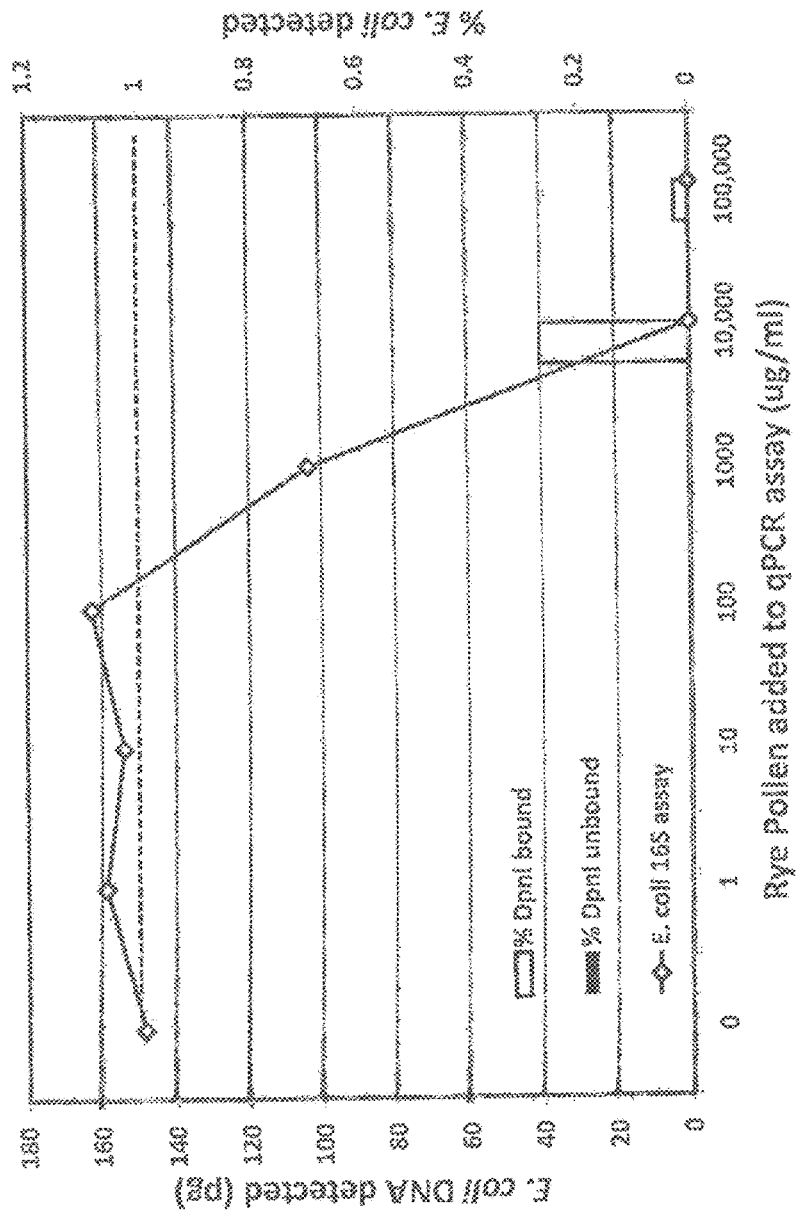

FIG. 24 demonstrates the effect of rye pollen on an *E. coli* 16S qPCR assay with and without DpnI enrichment. The quantity of *E. coli* DNA detected by a 16S qPCR assay was graphed as a function of pollen input (solid line), while the level of *E. coli* DNA remained constant (dashed line). Inhibitory levels of pollen (10,000 and 100,000 ug/ml) were then spiked into an *E. coli* sample that was segregated using DpnI. The amount of *E. coli* DNA detected in the bound ("% DpnI bound") and unbound ("% DpnI unbound") fractions is graphed as a percentage of the total amount of *E. coli* DNA.

DETAILED DESCRIPTION OF THE INVENTION

The present invention is directed to exploitation of epigenetic modifications specific to nucleic acids from a particular source. In one application; embodiments of the current invention can be used to separate and isolate prokaryotic DNA present in a sample that contains an excess of eukaryotic DNA. More specifically, embodiments of the current invention are directed to exploiting epigenetic modifications that are unique to prokaryotic DNA in order to selectively isolate and analyze the prokaryotic DNA found in a mixed sample.

In some embodiments, the invention relates to a method for segregating a target nucleic acid from a mixed sample containing the target nucleic acid and a non-target nucleic acid. In some embodiments, the method comprises contacting the mixed sample with a non-processive endonuclease or an antibody or antigen binding fragment thereof that binds the target nucleic acid (e.g., binds an epigenetic modification or methylation of the target nucleic acid). In some embodiments, the method comprises (i) contacting the mixed sample with a non-processive endonuclease or antibody or antigen binding fragment thereof that binds the target nucleic acid; and (ii) segregating a first fraction of the sample containing the complex from a second fraction of the sample containing the non-target nucleic acid. In some embodiments, the method comprises (i) contacting the mixed sample with a non-processive endonuclease or antibody or antigen binding fragment thereof that binds the target nucleic acid, wherein a complex of the non-processive endonuclease or antibody or antigen binding fragment thereof and the target nucleic acid is formed; and (ii) segregating a first fraction of the sample containing the complex from a second fraction of the sample containing the non-target nucleic acid. In some embodiments, the first fraction and the second fraction are retained. In some embodiments, the non-processive endonuclease binds the target nucleic acid, but does not cleave the target nucleic acid. In some embodiments, the method further comprises (iii) contacting the first fraction of (ii) with a non-processive endonuclease or antibody or antigen binding fragment thereof that binds the target nucleic acid; wherein the non-processive endonuclease binds the target nucleic acid, but does not cleave the target nucleic acid; wherein a complex of the non-processive endonuclease or antibody or antigen binding fragment thereof and the target nucleic acid is formed; and (vi) segregating a fraction containing the complex of (iii) from a fraction of the sample containing the non-target nucleic acid.

Other embodiments of the invention are related to a method for enriching a target nucleic acid in a mixed sample containing the target nucleic acid and a non-target nucleic acid. In some embodiments, the method comprises digesting the mixed sample with a methylation-sensitive or methylation-dependent endonuclease that cleaves the target nucleic acid and not the non-target nucleic acid, or incubating the mixed sample with an antibody or antigen binding fragment thereof that binds a epigenetic modification. In some embodiments, the method further comprises digesting the sample with an endonuclease; wherein the endonuclease cleaves the non-target nucleic acid and not the target nucleic acid, resulting in non-target nucleic acid ends that are incompatible with the cleaved target nucleic acid. In some embodiments, the method further comprises ligating a linker to the cleaved target nucleic acid, or circularizing the cleaved target nucleic acid. In some embodiments, the method further comprises depleting the non-target nucleic acid.

The invention also relates to compositions and kits for segregating a target nucleic acid from a mixed sample. In some embodiments, the compositions comprise (i) a mixed sample containing a target nucleic acid and a non-target nucleic acid and (ii) a non-processive endonuclease that binds the target nucleic acid, but does not cleave the target nucleic acid, or an antibody or antigen binding fragment thereof that binds the target nucleic acid. In some embodiments, the kits comprise (i) a biotinylated non-processive endonuclease that binds to the target nucleic acid, but does not cleave the target nucleic acid; and (ii) a buffer having conditions suitable for the non-processive endonuclease to bind the target nucleic acid, but not cleave the target nucleic acid. In some embodiments, the kits comprise a biotinylated non-processive endonuclease that recognizes methylated nucleic acid. In other embodiments, the kits comprise (i) a biotinylated non-processive endonuclease that binds to the target nucleic acid, but does not cleave the target nucleic acid, or a biotinylated antibody or antigen binding fragment thereof that binds to the target nucleic acid; (ii) a solid support material; and (iii) a binder specific for biotinylation. In some embodiments, the kits further comprise a methylated nucleic acid positive control.

Modification of DNA is found in all kingdoms. In pursuit of the current invention, various forms of DNA methylation were examined and it was noted that N4-methylcytosine (N4mC) and N6-Methyladenine (N6 mA) are found exclusively or predominantly in bacteria. N6 mA is of particular interest because it is found extensively in bacteria as a result of DNA Adenine Methylase (DAM) protein modification, although there are other adenine methylases present in prokaryotes. DAM is an essential adenine methylase found in bacteria including, but not limited to *Vibrio cholerae* and *Yersinia pseudotubercolosis*. Table 1 provides a non-comprehensive list of bacteria that demonstrate dam methylation. Many bacteria methylate at the N6 position of adenines within GATC sequences which occur approximately every 256 bases in the chromosome creating a ubiquitous target. Bacterial virulence is controlled via N6 mA including production of flagella, fimbrae, adhesion proteins, type II, III, and IV secretion, toxin synthesis and export. When the bacteria replicate their genome they can discriminate the nascent daughter strand from the parental via the absence of methylation. Thus, embodiments of the present invention exploit this mechanism by which bacteria recognize their own parental DNA, a function which is crucial to the survival and pathogenicity of bacteria where it has been studied. Detection of modified nucleotides other than N6 mA has been accomplished with antibodies previously.

TABLE 1

Thereat bacterial which use dam methylation

| Locus | Gene Symbol | Organism Name |
| --- | --- | --- |
| NT01BH4574 | dam | Bacillus halodurans C-125 |
| E2348_C_3631 | dam | Escherichia coli O127:H6 str. E2348/69 |
| Z4740 | dam | Escherichia coli O157:H7 EDL933 |
| NT03EC5148 | dam | Escherichia coli O157:H7 VT2-Sakai |
| ECH74115_4691 | dam | Escherichia coli O157:H7 str. EC4115 |
| RF_0123 | dam | Rickettsia felis URRWXCal2 |
| NT05SE2705 | dam | Salmonella enterica Paratyphi ATCC9150 |
| SPA3349 | dam | Salmonella enterica Paratyphi ATCC9150 |
| NT05SE3515 | dam | Salmonella enterica Paratyphi ATCC9150 |
| NT03ST1043 | dam | Salmonella enterica serovar Typhi CT18 |
| NT03ST3791 | dam | Salmonella enterica serovar Typhi CT18 |
| STY4312 | dam | Salmonella enterica serovar Typhi CT18 |
| NT03ST4828 | dam | Salmonella enterica serovar Typhi CT18 |
| t4022 | dam | Salmonella enterica serovar Typhi Ty2 |
| SeHA_C379O | dam | Salmonella enterica subsp. enterica serovar Heldelberg str. SL476 |
| NT01ST4356 | dam | Salmonella typhimurium LT2 SGSC1412 |
| STM3484 | dam | Salmonella typhimurium LT2 SGSC1412 |
| SO_0289 | dam | Shewanella oneidensis MR-1 |
| SBO_3374 | dam | Shigella boydii So227 |
| SDY_3692 | dam | Shigella dysenteriae Sd197 |
| S4357 | dam | Shigella flexneri 2a 2457T |
| AAN44857.1 | dam | Shigella flexneri 2a str. 3O1 |
| NT01SF4091 | dam | Shigella flexneri 2a str. 3O1 |
| SFV_3392 | dam | Shigella flexneri 5 str. B4O1 |
| SSO_3518 | dam | Shigella sonnei Ss046 |
| VC_2626 | dam | Vibrio cholerae El Tor N16561 |
| VC0395_A2203 | dam | Vibrio cholerae O395 |
| YpAngola_A3724 | dam | Yersinia pestis Angola |
| YPO0154 | dam | Yersinia pestis CO92 |
| NT01YP0175 | dam | Yersinia pestis CO92 |
| y3937 | dam | Yersinia pestis KIM |
| NT02YP4667 | dam | Yersinia pestis KIM |
| YP0156 | dam | Yersinia pestis biovar Medievalis 91001 |
| NT04YP0165 | dam | Yersinia pestis biovar Medievalis 91001 |

Based on these observations, some embodiments of the current invention utilize molecules that can exploit the presence of N6mA in bacteria. In one embodiment, an epigenetic-binder composition is provided that comprises an antibody or antigen binding fragment thereof directed to N6mA. Immuno-isolation of N6mA containing DNA is likely highly comprehensive for bacterial DNA given an average frequency of >1 N6 mA per KB in tested bacteria. In some embodiments, the antibody or antigen binding fragment thereof is an isolated antibody or antigen binding fragment thereof produced by the hybridoma cell line deposited under ATCC Deposit Designation Numbers PTA-13262 or PTA-13263. This provides a non-sequence specific target in bacterial DNA. The antibody or antigen binding fragment thereof can be optionally biotinylated or conjugated to allow for selective isolation. The use of an antibody or antigen binding fragment thereof as the epigenetic binder provides a more universal alternative as it is not dependent on a particular sequence motif (as is the restrictive enzyme embodiment) and therefore can be used against a wide range of bacterial generally carrying a particular epigenetic modification.

In some embodiments, the invention provides an antibody or antigen binding fragment thereof produced by a hybridoma cell line described in the examples and deposited at the American Type Tissue Collection (ATCC), 10801 University Boulevard, Manassas, Va., 20110-2209, as ATCC Deposit Designation PTA-13262, deposited with the ATCC on Oct. 2, 2012, and ATCC Deposit Designation PTA-13263, deposited with the ATCC on Oct. 2, 2012. In some embodiments, the invention provides a hybridoma cell line deposited at the ATCC under ATCC Deposit Designation PTA-13262, deposited with the ATCC on Oct. 2, 2012, and ATCC Deposit Designation PTA-13263, deposited with the ATCC on Oct. 2, 2012. In some embodiments, the invention provides an isolated antibody or antigen binding fragment thereof produced by the hybridoma cell line deposited under ATCC Deposit Designation Numbers PTA-13262 or PTA-13263. In some embodiments, the invention provides a hybridoma cell line deposited under ATCC Deposit Designation Numbers PTA-13262 or PTA-13263.

In some embodiments, the invention provides an isolated antibody or antigen binding fragment thereof which binds to substantially the same antigen as that which is bound by the antibody or antigen binding fragment thereof produced by the hybridoma cell line deposited under ATCC Deposit Designation Numbers PTA-13262 or PTA-13263. An isolated antibody or antigen binding fragment thereof which binds to substantially the same antigen as that which is bound by the antibody or antigen binding fragment thereof produced by the hybridoma cell line deposited under ATCC Deposit Designation Numbers PTA-13262 or PTA-13263 can be identified by methods known in the art. For example, pair-wise binding experiments test the ability of two antibodies or antigen binding fragments to bind simultaneously to the same antigen. Antibodies or antigen binding fragments thereof directed against separate epitopes will bind independently, whereas antibodies directed against identical or closely related epitopes will interfere with each other's binding. These binding experiments with BIACORE® are straightforward to carry out. For example, one can use a capture molecule to bind a first antibody or antigen binding fragment, followed by addition of antigen and a second antibody or antigen binding fragment sequentially. The sensorgrams will reveal: (1) how much of the antigen binds to the first antibody or antigen binding fragment, (2) to what extent the second antibody or antigen binding fragment binds to the surface-attached antigen, (3) if the second antibody or antigen binding fragment does not bind, whether reversing the order of the pair-wise test alters the results. Competitive ELISA experiments, described, e.g., in Example 6, also test the ability of two antibodies or antigen binding fragments to bind simultaneously to the same antigen. Itoh, K., M. Mizugaki, and N. Ishida, Preparation of a monoclonal antibody specific for 1-methyladenosine and its application for the detection of elevated levels of 1-methyladenosine in urines from cancer patients. Jpn J Cancer Res, 1988. 79(10): p. 1130-8.

In some embodiments, such antibodies or antigen binding fragments thereof are used in the methods, compositions and kits of the invention for segregation of a target nucleic acid from a mixed sample.

In other embodiments of the invention, a non-processive endonuclease is used in the methods, compositions and kits of the invention for segregation of a target nucleic acid from a mixed sample. As used herein, a "non-processive endonuclease" is an modified endonuclease having reduced or eliminated endonuclease activity. Examples of such modifications include, for example, a mutation of an endonuclease or buffer conditions which reduce or eliminate activity of an endonuclease. Examples of an endonuclease that can be non-processive include, for example, a restriction enzyme (e.g., DpnI), recombinase, resolvase, transposase, integrase, or repair enzyme. Further, a non-processive endonuclease of the invention is sensitive to epigenetic modifications when binding DNA (e.g., has methylation sensitivity).

In some embodiments, the non-processive endonuclease has, for example, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1% catalytic activity than an unmodified endonuclease, or any range of values thereof. In some embodiments, the non-processive endonuclease has, for example, from 10% to 0.01%, from 9% to 0.01%, from 8% to 0.01%, from 7% to 0.01%, from 6% to 0.01%, from 5% to 0.01%, from 4% to 0.01%, from 3% to 0.01%, from 2% to 0.01%, from 1% to 0.01%, from 10% to 1%, from 9% to 1%, from 8% to 1%, from 7% to 1%, from 6% to 1%, from 5% to 1%, from 4% to 1%, from 3% to 1%, or from 2% to 1% less catalytic activity than an unmodified endonuclease. Methods for determining the catalytic activity of non-processive endonuclease are known in the art and described herein.

In another embodiment, a restriction enzyme of the invention is adapted to selectively bind, but not cleave at subsequences carrying a specific epigenetic modification. The restriction enzyme activity is modified, for example, by removal of metal ion cofactors or alternatively, through amino acid point mutations of the protein itself. This allows selective binding of either DNA without an epigenetic modification (e.g. eukaryotic DNA without N6 mA) or with the desired epigenetic modification (bacterial DNA with N6 mA) for purification and analysis of fractions of interest. Table 2 provides a list of restriction enzymes and DNA protein binders with methylation specificity (Roberts, R. J., et al., *REBASE—a database for DNA restriction and modification: enzymes, genes and genomes*. Nucleic Acids Res. 38(Database issue): p. D234-6).

TABLE 2

Examples of restriction enzymes and DNA binding proteins with methylation specificity.

| Protein class | Class description | | Examples | Recognition substrate |
|---|---|---|---|---|
| Type II | The Type II restriction systems typically contain individual restriction enzymes and modification enzymes encoded by separate genes. The Type II restriction enzymes typically recognize specific DNA sequences and cleave at constant positions at or close to that sequence to produce 5' phosphates and 3' hydroxyls. Usually they require Mg2+ ions as a cofactor, although some have more exotic requirements. The methyltransferases usually recognize the same sequence although some are more promiscuous. Three types of DNA methyltransferases have been found as part of Type II R-M systems forming either C5-methylcytosine, N4-methylcytosine or N6-methyladenine. | Type IIM methyl directed Restriction enzymes | DpnI, CfuI, FtnUI, NanI | Gm6ATC |
| | | | MspI | m4CCGG |
| | | | MboI | GATm4C |
| | | | GlaI, GluI | Gm5CGm5C |
| | | | AoxI | GGm5CC |
| | | | MspJI | m5CNNRN$_{13}$ |
| | | Type II Blocked by CpG methylation | AciI | CCGC (−3/−1) |
| | | | BstUI | CG/CG |
| | | | HhaI | GCG/C |
| | | | HpaII | C/CGG |
| | | | HpyCH4IV | A/CGT |
| | | | PvuI | CGAT/CG |

TABLE 2-continued

Examples of restriction enzymes and DNA binding proteins with methylation specificity.

| Protein class | Class description | Examples | Recognition substrate |
|---|---|---|---|
| Type IVM Methyl directed restriction enzymes | These systems are composed of one or two genes encoding proteins that cleave only modified DNA, including methylated, hydroxymethylated and glucosyl-hydroxymethylated bases. Their recognition sequences have usually not been well defined except for EcoKMcrBC, which recognizes two dinucleotides of the general form RmC (a purine followed by a methylated cytosine either m4C or m5C) and which are separated by anywhere from 40-3000 bases. Cleavage takes place approximately 30 bp away from one of the sites. | EcoKMcrBC EcoKMcrA | $RmC(N)_{40-2000}RmC$ Y5mCGR |
| DNA binding proteins | Proteins which have low affinity for unmethylated DNA, and medium to high affinity for hemi and fully methylated DNA | CtrA SeqA | Gm6ANTC Gm6ATC |

In some embodiments, the non-processive endonuclease contains one or more mutations which cause the endonuclease to bind, but not cleave, a methylated nucleic acid recognition or cleavage site. In some embodiments, the mutation is in a cation binding motif of the endonuclease. In some embodiments, the non-processive endonuclease is a restriction enzyme having a mutation selected from the following Table 3.

TABLE 3

| Restriction enzyme | Mutation | % of WT cleavage activity | Citation |
|---|---|---|---|
| BamHI | G56S | 1 | Xu, S Y and Schildkraut, I. "Isolation of BamHI variants with reduced cleavage activities." JBC. 266 (7): 4425-4429. 1991 |
| | G91S | 1 | Xu, S Y and Schildkraut, I. "Isolation of BamHI variants with reduced cleavage activities." JBC. 266 (7): 4425-4429. 1991 |
| | T153I | 0.1 | Xu, S Y and Schildkraut, I. "Isolation of BamHI variants with reduced cleavage activities." JBC. 266 (7): 4425-4429. 1991 |
| | T114I | 1 | Xu, S Y and Schildkraut, I. "Isolation of BamHI variants with reduced cleavage activities." JBC. 266 (7): 4425-4429. 1991 |
| | G130R | 0.1 | Xu, S Y and Schildkraut, I. "Isolation of BamHI variants with reduced cleavage activities." JBC. 266 (7): 4425-4429. 1991 |
| | E135K | 1 | Xu, S Y and Schildkraut, I. "Isolation of BamHI variants with reduced cleavage activities." JBC. 266 (7): 4425-4429. 1991 |
| | T153I | 1 | Xu, S Y and Schildkraut, I. "Isolation of BamHI variants with reduced cleavage activities." JBC. 266 (7): 4425-4429. 1991 |
| | T157I | 1 | Xu, S Y and Schildkraut, I. "Isolation of BamHI variants with reduced cleavage activities." JBC. 266 (7): 4425-4429. 1991 |
| | G194D | 1 | Xu, S Y and Schildkraut, I. "Isolation of BamHI variants with reduced cleavage activities." JBC. 266 (7): 4425-4429. 1991 |
| | D94N | <0.1 | Xu, S Y and Schildkraut, I. "Isolation of BamHI variants with reduced cleavage activities." JBC. 266 (7): 4425-4429. 1991 |
| NaeI | T60I | <0.1 | Holtz, J K and Topal, M D. "Location of putative binding and catalytic sites of NaeI by random mutagenesis." JBC. 269(44): 27286-27290. 1994. |
| | E70K | <0.1 | Holtz, J K and Topal, M D. "Location of putative binding and catalytic sites of NaeI by random mutagenesis." JBC. 269(44): 27286-27290. 1994. |
| | G141D | 1-5 | Holtz, J K and Topal, M D. "Location of putative binding and catalytic sites of NaeI by random mutagenesis." JBC. 269(44): 27286-27290. 1994. |
| | D95N | 1-5 | Holtz, J K and Topal, M D. "Location of putative binding and catalytic sites of NaeI by random mutagenesis." JBC. 269(44): 27286-27290. 1994. |
| BsoBI | I95M | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |

TABLE 3-continued

| Restriction enzyme | Mutation | % of WT cleavage activity | Citation |
|---|---|---|---|
| | D124Y | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | G123R | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | D212N | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | K209R | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | D212V | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | D246G | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| | E252K | <0.1 | Ruan, H; Lunnen, K D; Pelletier, J J; Xu, S Y. "Overexpression of BsoBI restriction endonuclease in E coli, purification and recombinant BsoBI, and identification of catalytic residues of BsoBI by random mutagenesis." Gene. 188: 35-39. 1997. |
| Eco57I | D78N | <0.1 | Rimseliene, R and Janulaitis, A. "Mutational analysis of two putative catalytic motifs of the Type IV restriction endonuclease Eco57I." JBC. 276. 10492-10497. 2001. |
| | E92Q | <0.1 | Rimseliene, R and Janulaitis, A. "Mutational analysis of two putative catalytic motifs of the Type IV restriction endonuclease Eco57I." JBC. 276. 10492-10497. 2001. |
| EcoRV | Q69E | <0.1 | Vipond, I B and Halford, S E. "Random mutagenesis targeted to the active site of the EcoRV restriction endonuclease." Biocemistry. 35(6): 1701-1711. 1996. |
| | N70D | 0 | Vipond, I B and Halford, S E. "Random mutagenesis targeted to the active site of the EcoRV restriction endonuclease." Biocemistry. 35(6): 1701-1711. 1996. |
| | Y72N | <0.1 | Vipond, I B and Halford, S E. "Random mutagenesis targeted to the active site of the EcoRV restriction endonuclease." Biocemistry. 35(6): 1701-1711. 1996. |
| | P73A | <0.1 | Vipond, I B and Halford, S E. "Random mutagenesis targeted to the active site of the EcoRV restriction endonuclease." Biocemistry. 35(6): 1701-1711. 1996. |
| | P73T | 0 | Vipond, I B and Halford, S E. "Random mutagenesis targeted to the active site of the EcoRV restriction endonuclease." Biocemistry. 35(6): 1701-1711. 1996. |
| | D90N | 0 | Vipond, I B and Halford, S E. "Random mutagenesis targeted to the active site of the EcoRV restriction endonuclease." Biocemistry. 35(6): 1701-1711. 1996. |
| | I91L | <0.1 | Vipond, I B and Halford, S E. "Random mutagenesis targeted to the active site of the EcoRV restriction endonuclease." Biocemistry. 35(6): 1701-1711. 1996. |
| | K92R | 0 | Vipond, I B and Halford, S E. "Random mutagenesis targeted to the active site of the EcoRV restriction endonuclease." Biochemistry. 35(6): 1701-1711. 1996. |
| | T93A | <0.2 | Vipond, I B and Halford, S E. "Random mutagenesis targeted to the active site of the EcoRV restriction endonuclease." Biochemistry. 35(6): 1701-1711. 1996. |
| | E45A | <0.1 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |

TABLE 3-continued

| Restriction enzyme | Mutation | % of WT cleavage activity | Citation |
|---|---|---|---|
| | E45D | <0.3 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | E45Q | <0.3 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | P73A | 1 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D74A | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D74E | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D74N | 1.5 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D90A | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D90N | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | D90T | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | K92A | <0.1 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | K92E | <0.1 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| | K92Q | 0 | Selent, U; Ruter, T; Kohler, E; Liedtke, M; Thielking, V; Alves, J; Oelgeschlager, T; Wolfes, H; Peters, F; Pingoud, A. "A site-directed mutagenesis study to identify amino acid residues involved in the catalytic function of the restriction endonuclease E |
| FokI | D450A | | Waugh, D S and Sauer, R T. "Single amino acid substitutions uncouple the DNA binding and strand scission activities of FokI endonuclease." Proc Natl Acad Sci. 90: 9596-9600. 1993. |
| | D467A | | Waugh, D S and Sauer, R T. "Single amino acid substitutions uncouple the DNA binding and strand scission activities of FokI endonuclease." Proc Natl Acad Sci. 90: 9596-9600. 1993. |

In some embodiments, the non-processive endonuclease contains a motif selected from PD motif, D/EXK motif, H—N—H motif, or GIY-YIG motif.

In some embodiments, the non-processive endonuclease binds a recognition site with a methylated nucleic acid (e.g., has methylation specificity). In some embodiments, the non-processive endonuclease does not bind a recognition site with a methylated nucleic acid (e.g., does not have methylation specificity). In some embodiments, the non-processive endonuclease has specificity for N4-methylcytosine or N6-methyladenine.

The current invention also provides methods for utilizing epigenetic-binder compositions, non-processive endonucleases or antibodies with methylation specificity in order to separate and isolate a target nucleic acid population from a mixed sample. In one embodiment, the method involves applying an epigenetic binder to a mixed sample under conditions sufficient to form a complex with the target DNA. The complex can then be isolated from the mixed sample based on a variety of labels or physical properties imparted to the epigenetic binder. These include magnetic beads, beads which are sorted by optical properties, differential segregation of the nucleic acids based on the binding of protein as in an electrophoretic gel. More elaborate mechanisms of segregation would include mass spectrometry, FACS, acoustophoresis. It will be appreciated that a complex mixture can be segregated into multiple organismal DNA contributions by employing a multitude of labels.

In another embodiment, an epigenetic-specific digestion method is provided. The method includes applying an epigenetic-specific digestion factor to a sample under conditions sufficient to permit the factor to selectively cleave nucleic acid at a subsequence that is void of a particular epigenetic modification, wherein the epigenetic modification is present in the target nucleic acid. Following the epigenetic-specific cleavage, the non-target nucleic acid is depleted and the target nucleic acid is analyzed. In this embodiment, a mixed nucleic acid sample containing organisms from potentially any kingdom can be targeted for depletion of non-target DNA (eukaryotic or unwanted bacteria) and comprehensive amplification of selected bacterial genomes. In a preferred embodiment, the epigenetic-specific digestion factor is a restriction enzyme which selectively cuts a non-methylated recognition sequence thereby depleting the non-target DNA.

This embodiment involves four general steps. First, all DNA in a mixed sample is cut with a RE that is present in all genomes to generate a modest number of large fragments. Secondly adaptors are added to the fragments that contain universal priming sites and the fragments are ligated to form circles. Third, non target DNA is selected against by cutting with the attribute restriction endonuclease (i.e., KpnBI or DpnII) and treating with a linear specific DNAse (resulting in depletion of non-target DNA). Thus only nucleic acid which have the adaptor will have circular molecules at this stage. Fourth, target DNA is amplified with whole genome amplification or the adaptor universal primers.

Table 4 provides a list of example materials and additional modifications that could be employed in practicing the epigenetic-specific digestion method. It should be appreciated that there are multiple alternative approaches not listed herein for separating, isolating and amplifying the target DNA following the epigenetic-specific digestion of the non-target DNA.

TABLE 4

| Steps | Example Materials | Additional Considerations |
| --- | --- | --- |
| 1. Methylation selective digestion and optional linearization for adaptor ligation. Restriction enzyme which selectively cleaves non-methylated subsequences thereby selectively cutting non-target DNA. Target DNA specific cleavage for adaptor ligation. | See Table 5 below. DpnII- non-target specific endonuclease such as (cleaves only DNA unmethylated at GATC sites). BamHI- target specific endonuclease cleaves any GGATCC site - used if linearizing DNA for adaptor embodiment | a. Restriction enzyme combinations are chosen which leave target DNA with efficient ligation ends and clutter DNA with inefficient blunt or incompatible ends. b. Nesting of non-target cleavage sites within target cleavage sites is used to destroy target DNA cleavage sites when necessary (GATC is nested within GGATCC) c. Blunt ending of non-target molecules may need to be performed (Kleenow, T4 polymerase, Mungbean nuclease. |
| 2. Adaptor ligation/circularization of target molecules (alternative embodiment) Adaptor ligation into target DNA. Adaptor contains primer sequences for selective PCR amplification of target genome. (e.g., SEQ ID NOs: 1-9) | T4 ligase Synthetic adaptors: with flanking primer sites, ends adaptable to the target sequences. Note that variations on the adaptor include a variety of unique overhangs or blunt ends. Additionally the inclusion of synthetic nucleotides can aid in increased binding, resistance to exonucleases and the addition of methylated nucleotides offers additional differential digestion opportunities. | a. A molar excess of adaptor molecules is added to drive the ligation of adaptors. Sticky ended target molecules are driven to circularize. b. Synthetic adaptors can include nuclease resistant bases to aid in the selection of target molecules using only DNases (no dependence on circularization) when desired. |
| 3. Depletion of non-target DNA Reduce background non-target DNA to improve isolation and amplification | Plasmid-Safe DNase (EpiBio) DpnII- non-target specific endonuclease (cleaves only DNA unmethylated at GATC sites). | a. Gel electrophoretic based size selection (PFGE, SCODA, etc) which retains non-target DNA for analysis or; b. DNase digestion of non-target DNA based on: i. linear vs. circular and/or; |

TABLE 4-continued

| Steps | Example Materials | Additional Considerations |
|---|---|---|
| 4. Amplification of target DNA | See FIG. 1. | ii. adaptor protected vs. nonprotected<br>iii. Second restriction enzyme digestion of non-methylated DNA<br>a. PCR amplify bacterial DNA using primers in synthetic adaptors or;<br>b. Adaptor primer is used for rolling circle amplification of bacterial DNA or;<br>c. Whole genome amplification methods |

As provided in Step 1 above in Table 4, restriction enzyme combinations can be employed which selectively cut at unmethylated and methylated subsequences in order to selectively deplete the non-target DNA and additionally, permit selective insertion of the adapter in the target DNA. In one embodiment, this selectivity is performed by choosing a non-target specific restriction enzyme that cuts at a subsequence that is nested in the subsequence recognized by the target-specific restriction enzyme. Examples of suitable restrictive enzyme combinations to be use in this embodiment of the current inventive method are provided in Table 5.

TABLE 5

| Methylated sequence | Cut by | RE that will not cut | Comments |
|---|---|---|---|
| CGm6ATCG | PvuI | XorII, DpnII | PvuI cuts w/wo N6mA |
| Gm6ATC | FnuEI, Sau3AI, DpnI | MboI, NdeII, DpnII, BstKTI | |
| RGm6ATCY | BstYI, XhoII | MflI, DpnII | BstYI or XhoII cuts w/wo N6mA |
| TCCGGm6A | BspMi, Kpn2I, MroI | AccIII | |
| TCGCGm6A | AmaI, SalDI, Sbol3I, SpoI | NruI | |
| TTCGm6AA | CbiI | BstBI, Csp45I, SspRFI | |
| GGm6ATCC | BamHI | MboI, NdeII, DpnII, BstKTI | Nested site |
| GCGm6ATCGC | AsiSI, SgfI | MboI, NdeII, DpnII, BstKTI | Nested site |

As used herein, a mixed sample related to the invention contains a target nucleic acid and a non-target nucleic acid. In some embodiments, a mixed sample related to the invention contains at least one target nucleic acid and at least one non-target nucleic acid. In some embodiments, the target nucleic acid is prokaryotic nucleic acid (e.g., bacteria) or eukaryotic nucleic acid (e.g., human). In some embodiments, the mixed sample contains nucleic acid from at least two different prokaryotic organisms. In some embodiments, the mixed sample contains nucleic acid from human and bacterial organisms. In some embodiments, the mixed sample contains nucleic acid from eukaryotic and prokaryotic organisms. In some embodiments, the mixed sample contains nucleic acid from at least two different eukaryotic organisms. In some embodiments, the mixed sample contains nucleic acid from an unknown organism.

In some embodiments, the methods and compositions of the invention can additionally comprise an inhibitor. In some embodiments, the inhibitor can segregate into either the first fraction or the second fraction. As used herein, an "inhibitor" includes any compound which inhibits amplification of a nucleic acid from a mixed sample, including environmental or clinical contaminants, humic acid, diesel soot, or an inhibitor selected from the following Table 6 (Rådström, P. et al. (2004) Pre-PCR processing: Strategies to generate PCR-compatible Samples. Mol. Biotechnol. 26, 133-46).

TABLE 6

| Inhibitor | Source of Inhibitor | Reference |
|---|---|---|
| bile salts | feces | 9* |
| complex polysaccharides | feces, plant material | 10* |
| collagen | tissues | 11* |
| heme | blood | 12* |
| humic acid | soil, plant material | 13*, 14 |
| melanin and eumelanin | hair, skin | 15*, 16 |
| myoglobin | muscle tissue | 17* |
| polysaccharides | plants | 18* |
| proteinases | milk | 19* |
| calcium ions | milk, bone | 20* |
| urea | urine | 21* |
| hemoglobin, lactoferrin | blood | 22* |
| immunoglobin G (IgG) | blood | 23* |
| indigo dye | denim | 24 |

In some embodiments, a non-processive endonuclease of the invention binds to a target nucleic acid, but does not cleave the nucleic acid due to the in vitro buffer conditions of the method or composition. In some embodiments, the buffer contains a Mg2+ concentration suitable for the non-processive endonuclease to bind the target nucleic acid, but not cleave the target nucleic acid. In some embodiments, the Mg2+ concentration is, for example, less than 10 mM, less than 9 mM, less than 8 mM, less than 7 mM, less than 6 mM, less than 5 mM, less than 4 mM, less than 3 mM, less than 2 mM, less than 1 mM, or any range of values thereof. In some embodiments, the Mg2+ concentration is, for example, from 10 mM to 1 mM, from 9 mM to 1 mM, from 8 mM to 1 mM, from 7 mM to 1 mM, from 6 mM to 1 mM, from 5 mM to 1 mM, from 4 mM to 1 mM, from 3 mM to 1 mM, or from 2 mM to 1 mM. In some embodiments, the buffer does not contain Mg2+. In some embodiments, the buffer contains divalent cations. In some embodiments, the buffer contains Ca2+, Cd2+, Sr2+, Ba2+, Co2+, or Mn2+. In some embodiments, the Ca2+ concentration is, for example, at least 50 mM, at least 60 mM, at least 70 mM, at least 80 mM, at least 90 mM, at least 100 mM, or any range of values thereof. In some embodiments, the Ca2+ concentration is, for example, from 50 mM to 100 mM, from 60 mM to 100 mM, from 70 mM to 100 mM, from 80 mM to 100 mM, or from 90 mM to 100 mM. In some embodiments, the buffer contains a Ca2+ concentration that is, for example, at least 500 times greater, at least 600 times greater, at least 700 times greater, at least 800 times greater, at least 900 times greater, at least 1,000 times greater than the Mg2+ concentration of the buffer, or any range of values thereof. In some embodiments, the buffer contains a Ca2+ concentration that is from 500 to 1,000, from 600 to 1,000, from 700 to 1,000, from 800 to 1,000, or from 900 to 1,000 times greater than the Mg2+ concentration of the buffer. In some embodiments, the buffer contains a pH that inhibits endonuclease activity. A pH greater than 5 was shown to maximize binding to specific DpnI sequences relative to nonspecific sequences. Similar results have been observed by others (Engler et. al. (1997). Specific binding by EcoRV endonuclease to its DNA recognition site GATATC. J Mol Biol. 269(1):82-101.) While the rate of DNA catalysis decreases rapidly below pH 7 (Stanford et. al. (1999). DNA cleavage by the EcoRV restriction endonuclease: pH dependence and proton transfers in catalysis. J Mol Biol. 288(1):105-16. Thus pH values of 5-7 foster specific binding while reducing catalytic activity.

In some embodiments, the non-processive endonuclease or antibody or antigen binding fragment thereof of the invention comprises a detectable label. Examples of detectable labels include, for example, biotin, glutathione S-transferase (GST), polyhistidine (HIS), and digioxigenin.

In some embodiments, the methods, compositions or kits of the invention comprise a non-processive endonuclease or antibody or antigen binding fragment thereof bound to a solid substrate. Examples of solid substrates include, for example, a magnetic bead, a microtiter plate well, and a column surface.

In some embodiments, the methods, compositions or kits of the invention result in the segregated nucleic acid being, for example, at least 50%, at least 60%, at least 70%, at least 80%, at least 90%, at least 95%, or 100% of a target genome, or any range of values thereof. In some embodiments, the methods, compositions or kits of the invention result in the segregated nucleic acid being, for example, from 50% to 100%, from 60% to 100%, from 70% to 100%, from 80% to 100%, from 90% to 100%, or from 95% to 100% of the target genome.

In some embodiments, the methods, compositions or kits of the invention take, for example, less than 80 minutes, less than 70 minutes, less than 60 minutes, less than 50 minutes, less than 40 minutes, less than 30 minutes, less than 20 minutes, less than 10 minutes, or less than 5 minutes to complete, or any range of values thereof. In some embodiments, the methods, compositions or kits of the invention take, for example, from 80 minutes to 5 minutes, from 70 minutes to 5 minutes, from 60 minutes to 5 minutes, from 50 minutes to 5 minutes, from 40 minutes to 5 minutes, from 30 minutes to 5 minutes, from 20 minutes to 5 minutes, or from 10 minutes to 5 minutes to complete.

In some embodiments, the methods, compositions or kits of the invention result in, for example, less than 10%, less than 9%, less than 8%, less than 7%, less than 6%, less than 5%, less than 4%, less than 3%, less than 2%, or less than 1% of the non-target nucleic acid in the mixed sample being segregated into the first fraction, or any range of values thereof. In some embodiments, the methods, compositions or kits of the invention result in, for example, from 10% to 1%, from 9% to 1%, from 8% to 1%, from 7% to 1%, from 6% to 1%, from 5% to 1%, from 4% to 1%, from 3% to 1%, or from 2% to 1% of the non-target nucleic acid in the mixed sample being segregated into the first fraction.

In some embodiments, the methods, compositions or kits of the invention result in, for example, at least 50%, at least 60%, at least 70%, at least 80%, at least 90%, at least 95%, or 100% of the target nucleic acid in the mixed sample being segregated into the first fraction, or any range of values thereof. In some embodiments, the methods, compositions or kits of the invention result in, for example, from 50% to 100%, from 60% to 100%, from 70% to 100%, from 80% to 100%, from 90% to 100%, or from 95% to 100% of the target nucleic acid in the mixed sample being segregated into the first fraction.

In some embodiments, the mixed sample contains, for example, 5, 6, 7, 8, 9, 10, 20 or more logs of non-target nucleic acid, or any range of values thereof. In some embodiments, the mixed sample contains, for example, from 5 to 20 logs, from 6 to 20 logs, from 7 to 20 logs, from 8 to 20 logs, from 9 to 20 logs, or from 10 to 20 logs of non-target nucleic acid. In other embodiments, the mixed sample contains, for example, less than 10 pg; less than 9 pg; less than 8 pg, less than 7 pg, less than 6 pg, less than 5 pg, less than 4 pg, less than 3 pg, less than 2 pg, or less than 1 pg of target nucleic acid, or any range of values thereof. In some embodiments, the mixed sample contains, for example, from 10 pg to 1 pg; from 9 pg to 1 pg, from 8 pg to 1 pg, from 7 pg to 1 pg, from 6 pg to 1 pg, from 5 pg to 1 pg, from 4 pg to 1 pg, from 3 pg to 1 pg, or from 2 pg to 1 pg of non-target nucleic acid.

In some embodiments, the invention is directed to a method for isolating and detecting nucleic acid from a target organism in a sample containing nucleic acid from a target and non-target organism comprising the steps of: applying an epigenetic binder to the sample under conditions sufficient to permit the epigenetic binder to bind an epigenetic modification present in the nucleic acid of the target organism thereby forming an epigenetic binder-nucleic acid complex; isolating the epigenetic binder-nucleic acid complex from the sample; and purifying the nucleic acid present in the isolated complex. In some embodiments, the epigenetic modifications is a prokaryotic-specific epigenetic modification. In some embodiments, the epigenetic modification is selected from the group consisting of N4-methylcytosine, N6-Methyladenine, and sulfur modifications. In some embodiments, the epigenetic binder is a monoclonal antibody or antigen binding fragment thereof with affinity for nucleic acids carrying a N6-Methyladenine modification. In some embodiments, the epigenetic binder is a monoclonal antibody or antigen binding fragment thereof with affinity for nucleic acids carrying a N4-Methylcytosine modification. In some embodiments, the epigenetic binder is a biotinylated restriction enzyme. In some embodiments, the epigenetic binder is a monoclonal antibody or antigen binding fragment thereof with affinity for nucleic acids carrying a phosphorothioation modification. In some embodiments, the epigenetic binder is a restriction enzyme. In some embodiments, the conditions sufficient to permit the formation of the epigenetic binder-nucleic acid complex exclude the restriction enzyme cofactor in the reaction buffer. In some embodiments, the epigenetic binder is a non-cleaving mutant of a restriction enzyme. In some embodiments, the target organism is a prokaryotic organism. In some embodiments, the target organism is a bacterium. In some embodiments, the step of isolating the epigenetic binder-nucleic acid complex comprises the use of immunoprecipitation. In some embodiments, the step of isolating the epigenetic binder-nucleic acid complex comprises the use of gel retardation methods.

In some embodiments, the invention is directed to a method for isolating and detecting nucleic acid from a target organism in a sample containing nucleic acid from a target and non-target organism comprising the steps of: applying an epigenetic-specific digestion factor to a sample under conditions sufficient to permit the factor to selectively cleave nucleic acid at a subsequence that is void of a particular epigenetic modification, wherein the nucleic acid of the target organism contains the particular epigenetic modification at the subsequence and the nucleic acid of the non-target organism is void of the particular epigenetic modification at the subsequence; and isolation of the uncleaved nucleic acid of the target organism. In some embodiments, the method further comprises the step of applying a depletion factor to the sample under conditions sufficient to deplete substantially all of the nucleic acid of the non-target organism. In some embodiments, the particular epigenetic modification is selected from the group consisting of N4-methylcytosine, N6-Methyladenine, and phosphorothioation. In some embodiments, the target organism is prokaryotic and the non-target organism is eukaryotic.

A method for isolating and detecting prokaryotic nucleic acid in a sample containing both prokaryotic and eukaryotic nucleic acid comprising the steps of: applying an epigenetic-specific digestion factor to the sample under conditions sufficient to permit the factor to selectively cleave nucleic acid at a first subsequence that is void of a particular epigenetic modification, wherein the prokaryotic nucleic acid includes the epigenetic modification at the first subsequence and the eukaryotic nucleic acid does not include the particular epigenetic modification at the first subsequence; applying a non-epigenetic-specific digestion factor to the sample, wherein the non-epigenetic-specific digestion factor cleaves at a second subsequence, wherein the first subsequence is nested within the cleavage site of the second subsequence; inserting an adaptor cassette between the cleavage site of the second subsequence such that only nucleic acid that was not cleaved by the epigenetic-specific digestion factor can receive the adaptor, wherein the adaptor cassette contains embedded polymerase chain reaction primer sequences; applying a depletion factor to the sample to degrade nucleic acid that does not have the adapter cassette inserted; and amplifying the nucleic acid containing the adaptor cassette.

In some embodiments, the invention is directed to a composition for binding epigenetic modifications in prokaryotic nucleic acid comprising: a monoclonal antibody or antigen binding fragment thereof with affinity for nucleic acids carrying a N6-Methyladenine modification. In some embodiments, the monoclonal antibody or antigen binding fragment thereof is biotinylated.

In some embodiments, the invention is directed to a composition for binding epigenetic modifications in prokaryotic nucleic acid comprising: a restriction enzyme that selectively binds an epigenetic modification selected from the group consisting of N4-methylcytosine, N6-Methyladenine, and phosphorothioation, wherein amino acids of the cleavage region of the restriction enzyme have been modified to destroy cutting ability. In some embodiments, the restriction enzyme is biotinylated.

EXAMPLES

Example 1

This example provides a general protocol for practicing the epigenetic binder method of the current invention.

Materials
DNA mixture to be enriched for bacterial genomic DNA
Methyl binder
  Biotinylated DpnI binder
  Biotinylated αN6mA mAb
Resuspension buffer (TE or di water)
mAb Binding buffer (10 mM NaK pH7, 140 mM NaCl, 0.05% Triton X100)
Biotinylated DpnI Binding buffer (10 mM TrisHCl ph7.5, 100 mM NaCl, 0.1% Tween20)
SA-Dynabeads (Dynal Inc)
QiaQuick PCR purification kit (Qiagen, Valencia, Calif.)
Methods
Choose the mAb if you want to collect single stranded DNA with no sequence dependencies. Choose the DpnI binder if you want to work with double stranded DNA and your target has methylated GATC sites.
Additional reagents include: αN4mA mAb, and other biotinylated restriction enzymes which are anticipated to use the same basic protocol below.
Preparation of beads
  Couple DpnI binder to beads
  Wash beads
Preparation of DNA
  DNA is resuspended in TE buffer or water
  DNA is fractionated (sonication) on ice to around 5 KB. Other methods include enzymatic restriction etc and are dependent on downstream applications. Smaller fragments work fine for immunoprecipitation. An important variable is the number of binding sites per fragment. Binding saturation is anticipated at six methyl binding sites, which occurs in approximately 1.5 kb. Larger fragments ensure greater coverage of the genome
  5 ug of fractionated DNA is diluted into TE or water. Amount of DNA can certainly vary. Typical applications will use 0.5-10 ug of DNA.
  mAb binding ONLY STEP: DNA is rendered single stranded by heating for 10' in a boiling water bath and quenched on ice for 5 minutes.
  The DNA solution is mixed with 0.11 volume of 10× binding buffer.
Binding and elution of target DNA
  5 ug of methyl-binder (3:1 mass ratio is standard) is added to the DNA solution and incubated with mixing for one hour at room temperature.
  mAb binding improves with longer incubation times and performs well at 4 C.
  binder conjugated Beads are washed with binding buffer twice. DNA is released with proteinase K treatment for 3 hours to overnight at 50 degrees C. DpnI binder can also be quickly released thru changes in pH or ionic strength.
  Bound DNA is purified using QiaQuick PCR purification kit and eluted in TE buffer.
  Eluted DNA is analyzed as desired. We use real-time quantitative PCR.

Example 2

This example provides another general protocol for practicing a method of the invention.
Bead Preparation:
First, coated magnetic beads are prepared by resuspending magnetic beads by rotation or vortexing. The amount of magnetic beads required (a "working volume") is calculated based on number of samples needed using the formula: (# samples×20 ul)+10 ul=working volume. 20 uls of magnetic beads are required per sample. With multiple samples, beads can be prepared in bulk, although it is recommended to account for the volume loss due to pipetting when calculating the working volume of beads needed.

Next, a working volume of magnetic beads is transferred to a new tube and placed on a magnet for 1-2 min. The resulting supernatant is removed by aspiration with a pipette while the tube is on the magnet. The tube is then removed from the magnet and at least a working volume of wash buffer is added to the inside of the tube where the beads are collected and the mixture resuspended gently by rotation or pipetting. These magnetizing, aspiration, washing and resuspending steps are repeated twice for a total of 2 washes. After the second wash, the magnetic beads are resuspended in the same working volume of wash buffer. 1/10 of a working volume of biotinylated protein solution is then added and incubated for 30 minutes with gentle end-over-end rotation at room temperature (23°–25° C.), e.g. 16 rpm on New Brunswick TC-7. The tube is then placed in a magnet for 2-3 mins and the supernatant discarded by aspiration with a pipette while the tube is on the magnet. The coated beads are washed 2 times with a working volume of wash buffer following the magnetizing, aspiration, washing and resuspending steps above. The beads are then washed once and resuspended in a working volume of binding buffer and aliquotted into 20 ul per reaction tube.

DNA Preparation:

DNA is suspended in Tris EDTA (TE), water or similar buffer and aliquotted in 45 ul of DNA solution to 5 ul of binding buffer.

DNA Immobilization:

Reaction tubes of prepared beads are placed in a magnet for 2-3 mins and the supernatant discarded. The tubes are then incubated for 30 minutes with gentle end-over-end rotation at room temperature (23°–25° C.), e.g. 16 rpm on New Brunswick TC-7. The tubes are removed from the rotator and placed on a magnet for at least 2 minutes. While the tubes are on the magnet, the supernatant is removed by pipette (i.e., the Non-Target fraction). The beads are then washed twice with 200 ul of wash buffer following the magnetizing, aspiration, washing and resuspending steps above.

Bacterial DNA Elution (Optional Step):

Sample tubes are placed on a magnet for 2-3 mins and the supernatant discarded by aspiration with a pipette while the tube is on the magnet. 20 ul of elution buffer is then added to each sample and the samples vortexed for 5 minutes at room temperature. Next, the sample tubes are placed on a magnet for 2-3 mins and the supernatant removed by aspiration with a pipette. The above elution steps are repeated with a second 20 ul of elution buffer and combined to form the target fraction.

Desalting (Optional Step):

If downstream applications are sensitive to denaturing high-salt buffers, a desalting step is recommended using a desalting spin column per manufacturer's protocols.

Example 3

The following example provides data that one embodiment of the epigenetic-specific digestion method is effective to isolate bacterial DNA from a mixed sample. Example 3 utilizes steps 1 and 3 from Table 4 above.

1. Methylation Selective Digestion

A mixture was made of DNA from a eukaryotic organism, wheat (*Triticum aestivum*), and DNA from a bacterium (*Escherichia coli*)(Table 7). DpnII was used to digest DNA in the mixture containing only GATC sites unmethylated at the N6 position of adenine (Wheat DNA is restricted and not *E. coli*)(Table 7).

TABLE 7

| DNA mixture | | Mixture digestion | |
|---|---|---|---|
| 1.0 | 5 ng *E. coli* DNA | 2.0 | 10X DpnII buffer NEB |
| 7.0 | 6.0 ug Wheat genomic DNA | 2.0 | DpnII 10 u/ul |
| 8.0 | *E. coli*/wheat mixture | 8.0 | nuclease free water |
| | | 8.0 | *E. coli* and Wheat DNA mixture |
| | | 20.0 ul | |

Figure 2:
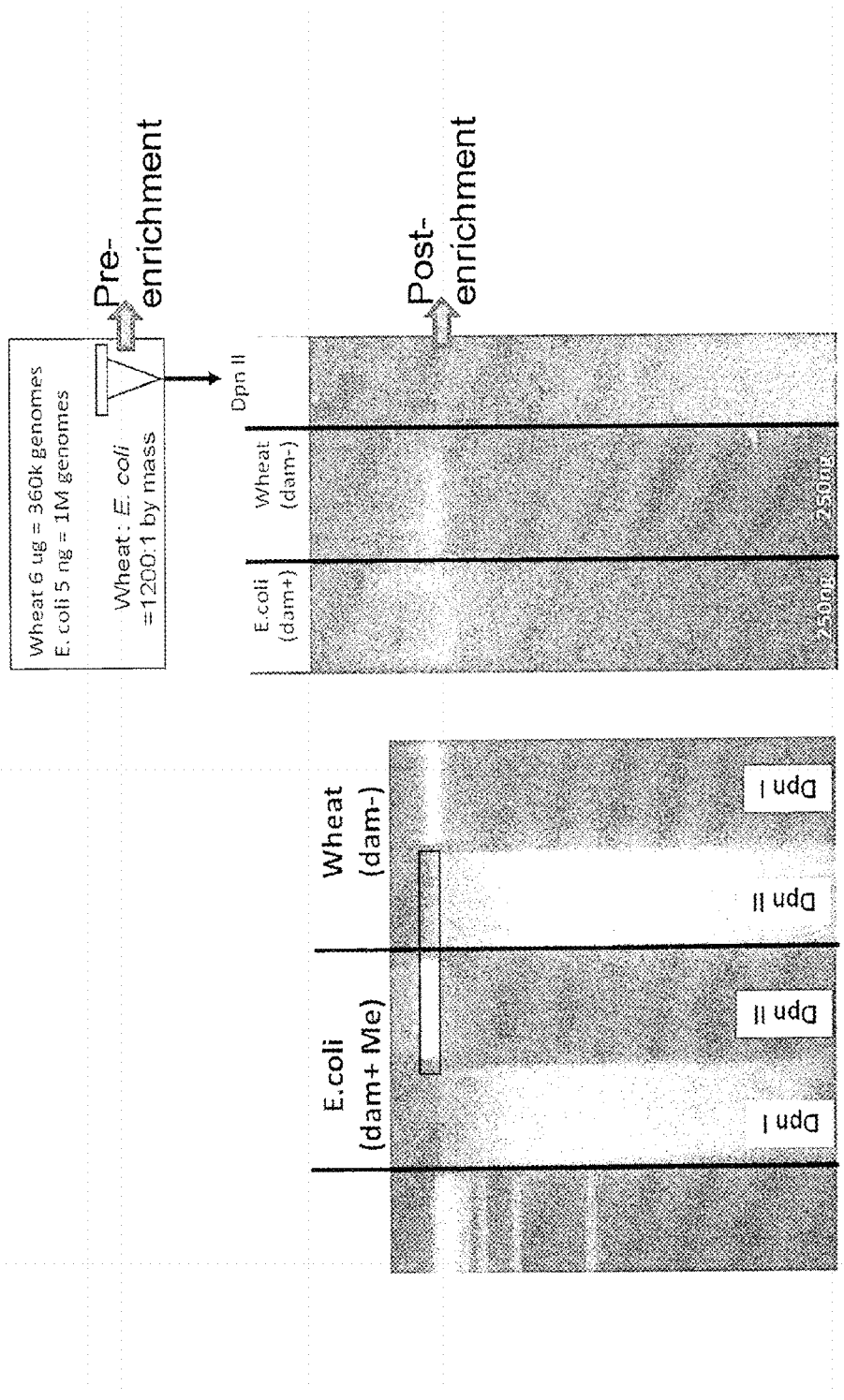
FIG. 2 shows methylation selective digestion enables segregation of prokaryotic (*E. coli*) and eukaryotic (Wheat) DNA. The left panel gel is 1.5% TAE agarose and has a molecular weight marker in lane 1. Lanes 2 and 3 have *E. coli* DNA (a bacterial dam+ organism) and lanes 4 and 5 have wheat DNA (a eukaryotic, dam-organism). DpnI (lanes 2 and 6) cuts only DNA methylated at adenines of GATC sites. DpnII (lanes 3 and 4) cuts only when GATCs are unmethylated. The right panel gel is also 1.5% TAE agarose. Lane 1 is 250 ng of *E. coli* DNA. Lane 2 is 250 ng of wheat DNA. Lane 3 is a mixture of 5 ng of *E. coli* and 6 ug of wheat DNA which is differentially restricted by DpnI digesting the wheat DNA. The resulting separation of wheat and *E. coli* DNA inputs enables segregation by size or compatibility of restricted ends. The arrows show the Pre-enrichment and Post-enrichment (gel isolated) samples that were sequenced.

FIG. 2 shows that methylation selective digestion enables segregation of prokaryotic and eukaryotic DNA. DpnI cuts only DNA methylated at adenines of GATC sites. DpnII cuts only when GATCs are unmethylated. A mixture of bacterial and eukaryotic DNA is differentially restricted enabling segregation by size or compatibility of restricted ends.

2. Depletion of Non-Target DNA

DpnII treated mixture was separated on a 1% agarose TBE gel for 2 hours at 50V. The band corresponding to the input DNA was isolated and extracted from the agarose slice using a Qiagen kit. Aliquots of the enriched and pre-enriched samples were prepared and sequenced on an Illumina GA-II.

Data Analysis 6,322,925 mappable sequence reads were obtained from the pre-enrichment sample. MegaBlast (NCBI) was used to assign 6,277,786 reads to wheat and 45,139 to *E. coli* or 0.7% *E. coli* reads in the initial mixture (FIG. 3). Following methyl selective digestion and depletion 5,430,392 mappable sequence reads were obtained. Surprisingly, 1,250,777 reads were from *E. coli* a full 23% or an apparent enrichment of 32 fold.

To specifically examine the efficiency of differential methylation digestion of eukaryotic DNA we counted the sequence reads which contained a GATC in each organism before and after purification. The fraction of bacterial reads with a GATC jumped from 10.2 to 75.6%. While the percentage of wheat reads with a GATC dropped from 89.76 to 24.4%. The data does not indicate why some wheat sequences remained uncut. The likely explanation is that the amount of enzyme used was insufficient to digest all 3 ug of wheat which suggests that the enrichment could be dramatically improved.

We observed an increase in the sequence coverage depth of *E. coli* from 0.24 to 6 fold with no clear biases (FIG. 4 A-D). The resulting coverage exceeds 99% (FIG. 4C) allowing clear identification of trace bacteria Example 4

The following example provides data that one embodiment of the epigenetic-specific digestion method is effective to isolate bacterial DNA from a mixed sample. Example 4 utilizes steps 1 through 4 from Table 4 above. Steps are shown on bacterial or human DNA individually (FIGS. 5-6), using a mixture of human and pUC19 DNA to achieve target DNA enrichment (FIG. 7) and using a mixture of human and *E. coli* DNA to achieve target DNA enrichment (FIG. 8). Restriction enzyme combinations were chosen which leave target DNA with efficient ligation ends and clutter DNA with inefficient blunt or incompatible ends. Nesting of non-target cleavage sites within target cleavage sites was used to destroy target DNA cleavage sites when necessary (e.g. GATC is nested within GGATCC). Blunt ending of non-target molecules may need to be performed (Klenow, T4 polymerase, Mung Bean nuclease).

1. Methylation Selective Digestion a) DpnII digestion of non-target DNA was performed according to Table 8.

TABLE 8

| Reagent | Concentration |
| --- | --- |
| DNA mixture | — |
| DpnII buffer NEB | 1x |
| DpnII | 1x |

Incubate at 37 degrees, 1 hour.
Heat inactivate 65 degrees, 20 minutes.
(see FIG. 2).

b) Blunt end DpnII overhangs were generated according to Table 9

TABLE 9

| Option 1. T4 DNA Polymerase | |
| --- | --- |
| Reagent | Concentration |
| DNA mixture | — |
| NEBuffer 2 | 1x |
| dNTPs | 100 uM |
| T4 DNA Polymerase | 1x. |

Incubate at 12 degrees, 15 minutes.
Heat inactivate

| Option 2. Mung Bean Nuclease | |
| --- | --- |
| Reagent | Concentration |
| DNA mixture | — |
| Mung Bean NEB buffer | 1x |
| Mung Bean Nuclease | 1x |

Incubate at 30 degrees, 30 mins.
Column clean to remove enzyme.

c) BamHi digestion of target DNA was performed according to Table 10.

TABLE 10

| Reagent | Concentration |
| --- | --- |
| DNA mixture | — |
| NEBuffer 3 | 1x |
| Bovine Serum Albumin | |
| BamHI | 1x |

Incubate at 37 degrees, 1 hour.
Column clean to remove enzyme.

2. Adaptor Ligation/Circularization

A molar excess of adaptor molecules is added to drive the ligation of adaptors. Sticky ended target molecules are driven to circularize (FIG. 5, 7).

a) Linkers were ligated according to Table 11.

TABLE 11

| Reagent | Concentration |
| --- | --- |
| DNA mixture | 1 pmol/ul |
| Annealed Linkers | 2-10 pmol/ul |

TABLE 11-continued

| Reagent | Concentration |
| --- | --- |
| T4 DNA Ligase Buffer | 1x |
| T4 DNA Ligase | 1x |

Incubate at 22 degrees, 10 minutes.
Heat inactivate at 65 degrees, 10 minutes.

FIG. 5 shows that adaptors (SEQ ID NO:1) ligated to sticky BamHI ends circularizes molecules and protects them from digestion enabling PCR amplification.

3. Depletion of Non-Target DNA

DNase digestion of non-target DNA based on; linear vs. circular molecules and/or adaptor protection (FIG. 6, 7).

a) Non-circular DNA was digested and re-digested with DpnII according to Table 12.

TABLE 12

| Reagent | Concentration |
| --- | --- |
| DNA mixture | — |
| PlasmidSafe Buffer ATP | 1x |
| PlasmidSafe Nuclease | 1x |
| DpnII | 1x |

FIG. 6 demonstrates selective digestion of linear versus circular DNA molecules which enables selective amplification of target molecules. DpnII restricted human genomic DNA (gDNA) is sensitive to plasmid safe DNAse (compare lanes 2 and 3) whereas circular molecules generated by adaptor ligation (lane 5, pUC19 control) are not.

4. Amplification of Targets

PCR amplify bacterial DNA using primers in synthetic adaptors (FIG. 5 lane 4) (FIG. 7 lane 12, FIG. 8 lanes 6 and 7).

a) The target DNA was PCR amplified according to Tables 13 and 14.

TABLE 13

| Reagent | Concentration |
| --- | --- |
| DNA mixture | 1 ul |
| Taq PCR Master Mix Kit (Qiagen) | 1x |
| Primer 1 (SEQ ID NO: 8) | 0.2 uM |
| Primer 2 (SEQ ID NO: 9) | 0.2 uM |

TABLE 14

| Step | | Temp | Duration |
| --- | --- | --- | --- |
| Initial denaturation | | 94 | 3 min |
| 3-step cycling, 25X | Denature | 94 | 1 min |
| | Anneal | 50 | 30 sec |
| | Extend | 72 | 3 min |
| Final extension | | 72 | 10 min |

FIG. 7 demonstrates that the epigenetic-specific digestion method with adaptor ligation is effective to isolate and amplify target DNA and degrade non-target DNA in a mixed sample. The lanes of the gel are as follows: Lane 1—linear KB ladder; Lane 2—human genomic DNA (hgDNA); Lane 3-1000:1 mixture containing 1 ng of pUC19 DNA (a surrogate for dam methylated bacterial DNA) in 1 ug of human genomic DNA; Lane 4—supercoiled pUC19. Methyl-selection was achieved by DpnII digestion and T4 polymerase blunting of ends followed by BamHI digestion, column purification and adaptor ligation mediated circularization. Samples of each template so treated are shown in lanes 5-8 revealing the smear of human DNA and preservation of bacterial DNA. Depletion of human DNA was achieved by Plasmid Safe DNAse and DpnII digestion (Lanes 8-9), which shows the removal of human DNA. Amplification with adaptor specific primers shows the amplification of the input pUC19 (Lane 13) even from the digested mixture (Lane 12) but not from human only DNA (Lane 11). Template negative controls of unprocessed hgDNA (Lane 14), unprocessed pUC19 (Lane 15) or no template do not generate an amplified signal.

FIG. 8 demonstrates that the epigenetic-specific digestion method with adaptor ligation is effective to isolate and amplify a target genome and degrade a non-target genome in a mixed sample. The lanes of the gel are as follows: Lane 1—linear KB ladder; Lane 2—human genomic DNA (hDNA); Lane 3—*E. coli* genomic DNA (*E. coli* gDNA); Lane 4—pUC19; Lane 5—human genomic DNA (hDNA) after epigenetic specific digestion and amplification; Lane 6—mixed human genomic DNA and 10 ng *E. coli* DNA (hDNA+10 ng Ec) after epigenetic specific digestion and amplification; Lane 7—10 ng *E. coli* genomic DNA (10 ng Ec gDNA) after epigenetic specific digestion and amplification; Lane 8—pUC19 after epigenetic specific digestion and amplification.

FIG. 9 quantifies the level of enrichment from a complex mixture. The initial mixture included approximately 100 pg of *E. coli* DNA and 1 ug of Human DNA or a 1 in 10,000 ratio). qPCR measurements were made on the DNA using the DYZ locus present in the male DNA (vertically striped bars) and the 16S locus present in *E. coli* (horizontally striped bars). After epigenetic specific digestion and amplification qPCR measured a ratio of 1:0.3, bacterial DNA: human, a 33,000× enrichment.

Example 5

The following example provides data that one embodiment of the epigenetic-specific digestion method is effective to isolate bacterial genomic DNA from a mixed sample. Example 5 utilizes steps 1 through 4 from Table 4 above. Restriction enzyme combinations were chosen which leave target DNA with efficient ligation ends and clutter DNA with incompatible ends. First Non-target genomes were cut with BstKI (does not cut bacterial GATC sites methylated at adenines). Then bacterial DNA is cut with Sau3AI, leaving a sticky ends at GATC sites of bacteria. The added linkers are specific only to the bacterial Sau3AI ends protecting the bacterial fragments from the subsequently added exonuclease. Amplification occurs from the sites embedded in the linkers.

1. Anneal linkers: GATC-4 nt sense and antisense
   a. Add 5 ul each S and A to 90 ul
   b. Heat 5 min @ 95 degrees
   c. Cool slowly in heat block to room temperature.
2. BstKT1 digest (blocked by Dam methylation—will not cut *E. coli*)
   a. DNA samples were prepared according to Table 15—human only (1), human+*E. coli* (2), and *E. coli* only (3).

TABLE 15

| Reagent | 1<br>hDNA | 2<br>hDNA + E. coli | 3<br>E. coli |
|---|---|---|---|
| hDNA (717 ng/ul) [1 ug] | 1.4 | 1.4 | — |
| pUC19 (dilute to 10 ng/ul) | — | 1 | 1 |
| 10x SEBuffer W | 1 | 1 | 1 |
| BstKTI (SibEnzyme #E151) | 1 | 1 | 1 |
| Water | 6.6 | 5.6 | 7 |
| Total Volume | 10 | 10 | 10 | b. Digest 60 min at 37 degrees.
   c. Heat inactivate 65 degrees, 20 min.
3. Sau3AI digest (produces GATC 5' overhang)
   a. Reactions were prepared according to Table 16.

TABLE 16

| Reagent | 1x | 3.5x |
|---|---|---|
| DNA | 10 | |
| 10x NEB1 | 1.5 | 5.25 |
| Sau3AI | 1.5 | 5.25 |
| 10x BSA | 1.5 | 5.25 |
| Water | 0.5 | 1.75 |
| Total volume | 15 | | b. Add 5 ul per reaction.
   c. Incubate at 37 degrees, 60 minutes.
   d. Heat inactivate 20 min A 65 degrees.
4. Ligate linkers
   a. Cutting 1 ng of MG1655 DNA with BstY1 leaves 1.04E-03 pmol of molecules, or 1.04 fmol of DNA.
   b. For 50:1, need 52 fmol linkers
   c. Linkers were diluted from 5 pmol/ul to 10 fmol/ul (1:50 in tris or DI) according to Table 17.

TABLE 17

| Reagent | 1x | 3.5x |
|---|---|---|
| DNA | 15 | |
| Inserts | 5 | 17.5 |
| 2x Quick Ligation Reaction buffer | 20 | 70 |
| Quick T4 DNA ligase | 1 | 3.5 |
| Total volume | 41 | | d. Incubate 5 min at room temp.
   e. Heat inactivate 65 degrees, 10 minutes.
5. ExoIII digest
   a. The following components of Table 18 were combined and added to the DNA—10 ul/tube

TABLE 18

| Regent | 1x | 3.5x |
|---|---|---|
| DNA | 41 | |
| 10x ExoIII buffer | 5 | 17.5 |
| ExoIII enzyme | 1 | 3.5 |
| Water | 3 | 10.5 |
| Total Volume | 50 | | b. Incubate at 37 degrees, 30 min.
   c. Heat inactivate 15 min at 65 degrees.

6. Amplification of the samples was performed by PCR according to Table 19.
   a. control)
   b. Only need the MeR (reverse) primer
   c. Samples:
      1. hDNA processed
      2. hDNA+*E. coli* processed
      3. *E coli* processed

TABLE 19

50x reverse primer mix (10 uM primer + water)

| Component | Volume | End condentration | Final conc in rxn |
|---|---|---|---|
| MeF- forward | 0 | 0 | 0 |
| MeR - reverse | 10 ul | 10 uM | 0.2 uM |
| Water | 90 | | |

| | Master Mix | 50x Primer Mix | DiWater | DNA | Total Volume |
|---|---|---|---|---|---|
| 1 | 50 | 2 | 38 | 10 | 100 |
| 3.5 | 175 | 7 | 133 | | 350 |

PCR reaction:

| Step | | Temp | Duration |
|---|---|---|---|
| Initial denaturation | | 94 | 3 min |
| 3-step cycling - | Denature | 94 | 30 sec |
| 25 cycles | Anneal | 50 | 30 sec |
| | Extend | 72 | 3 min |
| Final extension | | 72 | 3 min |

Results.

The results in FIG. 9 show that the initial sample mixture had a measured level of approximately 1 ug of human DNA and just over 100 pg of *E. coli* DNA when tested with qPCR. After the epigenetic selective amplification there was a dramatic reduction in the levels of human DNA (less than 10 pg) and amplification of bacterial DNA (over a ng). In this example amplification was kept to a modes 25 cycles, but it is appreciated that a greater level of amplification is possible. The change in the ratio of *E. coli* to human DNA of 1:10,000 changed by approximately 33,000 fold to 1; 0.3. This demonstrates a high level of enrichment that is particularly unique in the selective degradation of the high background of human DNA.

Example 6

The following example provides data to demonstrate the operability of an epigenetic binder to isolate bacterial DNA from a mixed sample. Specifically, gel retardation was used to determine if an epigenetic binder, restriction enzyme DpnI, was binding in a methyl-specific fashion and to ensure that binding conditions would not enable DNA restriction. The results provided herein depict methyl-specific binding of DpnI without DNA cleavage.
Materials
   699 ng/ul Biotinylated FLIR DpnI
   10 units/ul DpnI (NEB)
   1 KB ladder (Bioline)
   3% agarose gel in TBE
   Binding buffer
   Restriction buffer
   NEB Buffer 4
   Cation: 10 mM $Mg^{-+}$ or 10 mM $Ca^{++}$
150 ng DpnI or 20 units NEB DpnI
10x binding buffer
mM cation (where listed)
deionized water to final volume
100 ng pUC19 DNA
Methods DpnI was added to a 20 ul solution containing variants of the binding buffer, and a DNA template pUC19. Binding buffers included a final concentration of either $Mg^{++}$ or $Ca^{++}$ as listed. N6 mA pUC19 was methylated at GATC sites by passage in the $dam^+$ strain, MG1655, while unmethylated pUC19 was passaged in a $dam^-$ strain BL21. DpnI was incubated with pUC19 for two hours at either room temperature for binding or 37° C. for digestion. The reactions were carefully loaded onto agarose gels. The protein-DNA complexes were separated from unbound DNA by standard agarose gel electrophoresis. At the conclusion of the experiment, the gel was imaged using an Alpha Imager HP from Cell Biosciences.
Results The results in FIG. 10 demonstrate that under modified conditions, restriction enzymes can selectively bind N6 mA without cutting. First, substituting Ca++ for Mg++ led to binding of the N6 mA pUC19 as demonstrated by the gel retardation in a dose-dependent manner. For example, at 400 ng DpnI, all DNA is complexed with DpnI as evidenced by the retention in the well. Whereas, in the absence of DpnI, there is no gel retardation and the DNA has migrated accordingly. In contrast, when Mg++ is substituted into the reaction, DpnI cuts at N6 mA pUC19 as evidenced by the multiple bands. As demonstrated in the right panel of FIG. 10, the binding effect of DpnI is specific to N6 mA as gel retardation was not demonstrated with the unmethylated DNA (pUC19). Taken together, these results demonstrate that under the proper conditions, restriction enzymes can be used to specifically bind epigenetic modifications without cleavage. This provides evidence that restriction enzymes could be used as epigenetic binders to separate and isolate prokaryotic DNA from a mixed sample. Furthermore, modifications can be made to the restriction enzyme in order to aid in isolation of the restriction enzyme-DNA complex such as biotinylation or other conjugations.
Biotinylation of DpnI Purified DpnI was biotinylated (bDpnI) because commercially-available preparations are often only partially purified and contain high amounts of added bovine serum albumin (BSA). A HABA assay resulted in an incorporation of 2.8 biotins per DpnI molecule. Primer sets were used to generate two DNA fragments of 477 bp and 651 bp in length that overlap the same six GATC sites from pUC19. The fragments were unmethylated after PCR amplification as verified by methyl sensitive MboI restriction digestion. Dam methyltransferase (DMT) was used to methylate the 477 bp fragment (M477) turning it into a substrate for DpnI.

The biotinylated form of DpnI (bDpnI) was used in a binding reaction with a mixture of both unmethylated 651 bp and M477 fragments. bDpnI selectively reduced gel migration of the M477 fragment, indicative of methyl-specific DNA binding (FIG. 11).
Activity of Biotinylated DpnI on Avidin Coated Beads Next, the performance of bDpnI was evaluated for binding in the solution phase. 400 ng of bDpnI was incubated with 200 ng each of the M477 bp and the unmethylated 651 bp fragment (unM651) fragments for 1 hour. Avidin coated beads were then added and an additional hour of incubation was performed. The beads were magnetically collected, the supernatant saved, and the beads washed. The fractions were then run on a 3% agarose gel (FIG. 12). The supernatant exclusively contained the unM651 bp fragment, while the bound fraction contained both DNA products. This lower specificity can likely be addressed by altering the binding conditions.

In contrast, the specificity was excellent when bDpnI was prebound to beads. Increasing amounts of bDpnI-beads were added to the mixed unM651 and m477 bp fragments. After a 30 minute incubation, samples from the nontarget or target fractions were loaded on a gel for analysis. The nontarget fraction specifically lost the m477 bp fragment with increasing levels of bDpnI beads. The target fraction exclusively contained the m477 fragment (FIG. 13).

Specificity of Bacterial DNA Isolation from Genomic Mixtures

To determine the limits of bacterial DNA specificity, *E. coli* genomic DNA was titrated from 10 ng down to 1 pg in a background of 1 ug of human DNA to generate a series of genomic mixtures which was then incubated with bDpnI beads. In this protocol, the beads were washed one time, and the target and non-target fractions collected and then tested for the levels of human and *E. coli* DNA in each fraction. Recovery was assessed with qPCR to bacterial 16S and human DYZ, each normalized to their respective marker frequency. Approximately 10% of the human DNA was consistently recovered in the target fraction. No less than 30% of *E. coli* DNA was recovered at the pg level, while over 80% of *E. coli* was recovered with 10 ngs of input.

To determine the minimum time of bDpnI-bead and DNA incubation, a mixture of 1 ug of human and 500 pg of *E. coli* DNA was tested at 5 to 60 minutes of incubation time. In this protocol, three washes of the bDpnI-bead DNA complexes were used and the fractions were then tested with qPCR for DYZ and bacterial 16S rDNA. Recoveries were consistent across the measured incubation times (FIGS. 14 and 15). Additionally, binding of nontarget human DNA was reduced to 1% (FIGS. 14 and 15). In other experiments, human DNA binding was observed to increase with extended incubation times.

Coverage of Genome Recovery

In order to evaluate global genome recovery efficiency, a mixture of bacteria was prepared and sequenced before and after DpnI bead enrichment. The sample contained *Bacillus atrophaeus, Pseudomonas aeruginosa, E. coli* and two viruses; *Autpgrapha californica* nuclear polyhedrosis virus (AcNVP) and phage lambda. The mixture was considered relevant for evaluation of DpnI enrichment because it included organisms for which no enrichment (*Bacillus*), partial enrichment (*Pseudomonas*), and full enrichment (*E. coli*) were expected based on the presence of the Dam ($G^m$ATC) DNA motif.

The cell/virus mixture was then used for DpnI enrichment and the subsequent DNA prepared for next generation sequencing using a HiSeq. A summary of these data are shown in FIG. 16. A 14× enrichment of *E. coli* was observed with excellent coverage (FIG. 17), and key physical characteristics of the genome coverage were also maintained. Such characteristics include the ratio of coverage between the Origin of replication (OriC) and the Terminus. A ratio of 1 is indicative of an organism in stationary phase, while high ratios (4, 8, 16 and 32) represent increasingly rapid growth. Such information is important in evaluating the source and method of growth for a threat organism. The low coverage biases and maintenance of physical coverage features during the enrichment process are highly desirable. It should be noted that the coverage spikes are artificial, and that the high coverage occurs because bacteriophage (DLP, Rec and Qin) are present in other bacteria from this mix, leading to a false inflation.

Example 7

The following example shows the characterization of an initial polyclonal sera raised against N6-Methyladenosine (N6 mA) on a panel of bacteria focused on biothreats and representative eukaryotes. Adenine methylation is a discriminator of bacterial DNA from common eukaryotic genomes, but some pathogens do not present detectable adenine methylation. This example demonstrates the potential for immunoprecipitation as well as establishing a set of monoclonal antibodies. These methods can also be used for identifying the adenine methylation status of organisms and for general enrichment of bacterial genomes.

Materials and Methods

Immunogen, Conjugates, and DNA Samples.

N6-Methyladenosine 5'-monophosphatesodium salt, N6-Methyl-2-deoxyadenosine and 2-Deoxyadenosine 5-monophosphate, bovine serum albumin (BSA) and keyhole limpet hemocyanin (KLH) were purchased from Sigma-Aldrich (St. Louis, Mo.). Conjugation of KM to N6-Methyladenosine 5'-monophosphate sodium salt (N6 mA-KLH) as the immunogen and BSA conjugation to N6-Methyladenosine 5'-monophosphate sodium salt (N6 mA-BSA) for counter screening was performed as previously described. Erlanger, B. F. and S. M. Beiser, Antibodies Specific for Ribonucleosides and Ribonucleotides and Their Reaction with DNA. Proc Natl Acad Sci USA, 1964. 52: p. 68-74. Genomic DNA was purchased for Human male (Zyagen, San Diego, Calif.), and isolated from *E. coli* MG1655 (ATCC) using standard DNA extraction protocols (Qiagen, Germantown, Md.).

Antibody Production and Screening.

N6-Methyl adenosine 5'-monophosphate sodium salt was conjugated to KLH and used as the antigen. Erlanger, B. F. and S. M. Beiser, Antibodies Specific for Ribonucleosides and Ribonucleotides and Their Reaction with DNA. Proc Natl Acad Sci USA, 1964. 52: p. 68-74. Immunization of nine Balb/c mice was performed as previously described. Reynaud, C., et al., Monitoring of urinary excretion of modified nucleosides in cancer patients using a set of six monoclonal antibodies. Cancer Lett, 1992. 61(3): p. 255-62. Pre-immune bleeds and test bleeds were collected after each immunization for monitoring by indirect ELISA and competitive ELISA using N6-Methyl-2-deoxyadenosine and 2-Deoxyadenosine 5-monophosphate. Established procedures were used to produce hybridomas with SP2/0 cells and the resulting fusions rescreened as above. Shulman, M., C. D. Wilde, and G. Kohler, A better cell line for making hybridomas secreting specific antibodies. Nature, 1978. 276 (5685): p. 269-70.

Direct nucleotide ELISA were performed to titer the antibody, Wells were coated with 100 ul of a 1 ug/ml N6-Methyladenosine 5'-monophosphate sodium salt-BSA conjugate in Phosphate Buffered Saline (PBS), pH 7.4. Detection was accomplished with a HRP-conjugated goat anti-mouse IgG (Jackson Labs Technologies, Inc., Los Gatos, Calif.). The titer was identified from the highest dilution where the OD of the sample was 2.1 fold greater than the blank.

Competitive ELISA were performed as previously described. Itoh, K., M. Mizugaki, and N. Ishida, Preparation of a monoclonal antibody specific for 1-methyladenosine and its application for the detection of elevated levels of 1-methyladenosine in urines from cancer patients. Jpn J Cancer Res, 1988. 79(10): p. 1130-8. Wells were coated with the N6 mA-BSA conjugate ensuring that binding activity was not directed against the KLH component of the immunogen. Specificity was determined by incubating the antisera with either N6-Methyl-2-deoxyadenosine (specific inhibitor for the desired activity) or 2-Deoxyadenosine 5-monophosphate and adding it to the coated well. When antisera bound to the coated well, no competition was present.

Oligonucleotide ELISAs were performed using two oligos (TriLink Biotechnologies, Inc., San Diego, Calif.) with the following sequence: GCAGGATCAACAGTCACACT, where the underlined adenine was either unmethylated in one set or N6-methylated in another. Each oligo was mixed with equal volumes of Reacti-Bind DNA Coating Solution (Thermo Fisher Scientific, Waltham, Mass.) in glass tubes at a final DNA concentration of 8 µg oligo/ml. 100 ul of this coating mixture was transferred to wells in a 96-well round-bottom EIA plate and incubated at room temperature for two hours on an orbital mixer. The incubation was followed with three washes with wash buffer (TBS and 0.05% Tween-20) and subsequently blocked with 200 µl blocking solution (TBS, 0.05% Tween-20, and 1% BSA) per well for one hour at room temperature. After removal of the blocking solution, the wells were incubated for one hour with 100 µl blocking solution containing anti-methyl adenine mouse polyclonal antisera (at a 1:10,000 dilution), washed three times with wash buffer, then incubated with HRP-conjugated goat anti-mouse IgG (Jackson Labs) in blocking solution for 30 minutes. Non-bound antibodies were removed with three washes with wash buffer and then the ELISA was developed with 100 µl 1-Step Ultra TMB-ELISAs solution (Thermo Scientific) per well. The enzymatic reaction was terminated after 15 minutes with 100 µl 2M sulfuric acid and the color formed was measured at absorbance 450 nm. To perform genomic DNA ELISAs oligos were substituted with DNA at the concentrations listed in each experiment.

Results

Immune reactions were strong in all mice tested, requiring dilutions of up to 100,000 fold. The specificity of all sera was tested by comparing the reactivity to both Adenine and N6-methyl-Adenine (FIG. 19). We observed that only 100 ng of N6 mA resulted in 50% inhibition of sera binding to N6 mA coated ELISA plates. For comparison, 10 ug of Adenine (a 100 fold increase in reagent) resulted in about 30% inhibition. The final bleeds from 1,4, 8 and 9 were chosen to generate fusions.

Approximately 500 fusions were screened and after sub-cloning, and 16 hybridomas were identified with specificity to N6 mA in a primary direct nucleotide ELISA (two of which were deposited under ATCC Deposit Designation Numbers PTA-13262 and PTA-13263). The final bleeds and the 16 hybridomas were then tested using oligo ELISA (FIG. 19). All of the tested polyclonal sera have preferences to N6 mA of greater than 10 fold, and one hybridoma demonstrated nearly 40 fold discrimination for N6 mA in relation to the unmethylated oligo.

Polyclonal sera were further evaluated to compare their reactivity to DNA extracted from E. coli to human (FIG. 20). Genomic ELISA was used and titrated the amount of genomic DNA coating the wells for these tests. Differential sensitivity to bacteria was observed with genomic DNA above 6 ng.

Example 8

The following example provides data that embodiments of the invention using non-processive endonucleases for DNA isolation, segregates bacterial genomes away from PCR inhibitors. Environmental samples were collected including humus soils and ocean and polluted water samples during a San Diego rainstorm in locations of urban runoff, hematite coated sand, volcanic mud containing gypsum, and river bed silt from a high mineral content area of Utah. The ability to enrich bacterial DNA from diverse and often difficult sample types known to be high in inhibitors of PCR was evaluated.

Samples were processed using a MoBio kit to isolate total DNA, followed by DpnI-beads to generate an enriched Target fraction of γ-proteobacterial genomes and a NonTarget fraction of other genomes using the protocol in Example 2. The original sample and all subsequent fractions were evaluated for diversity using universal 16S primers. The work flow is summarized in FIG. 21. A summary of sample types and the results of 16S amplification are listed in Table 20.

TABLE 20

Sample types tested for PCR inhibition alleviation using DpnI segregation

| Sample type | Amplifiable post MoBio DNA isolation | Amplifiable post DpnI segregation |
|---|---|---|
| 2 residential soils | 2 No | Yes |
| 1 hematite sand | 1 No | Yes |
| 1 riverbed silt/sediment | 1 No | Yes |
| 5 water samples | 4 Yes, 1 partial | Yes |
| 1 ocean air | 1 Yes | Yes |

Most water samples and the air sample generated 16S amplicons indicative of the presence of bacteria. The urban brackish river sample amplified poorly and no 16S amplification was seen from either of the humus soil samples, the sand, mud or silt. In every case where the MoBio isolated DNA did not generate a 16S profile, neither did the unbound fraction. However, the bound target fraction was free of inhibition and demonstrated the presence of bacteria from microenvironments that were frequently free of visible plant, animal or bacterial growth.

FIG. 22 shows that the non-target DNA fraction from two humus soil samples does not amplify. The presence of PCR inhibitors was implicated when E. coli DNA spiked into the soil samples did not amplify in comparison to E. coli DNA alone. However, target fractions showed no inhibition and, in fact, revealed a high diversity of 16S bands. While the initial diversity of soil samples cannot be evaluated, nor can the NonTarget fraction. As such, useful information was obtained from sample types that were previously inaccessible.

FIG. 23 shows that the DNA isolated directly with a MoBio kit was not amplifiable with 16S primers from soil samples (silt, sand and volcanic mud). These samples are known to be high in salts, hematite and gypsum, respectively. Following DpnI segregation, all samples were amplifiable.

Example 9

The following example provides data that embodiments of the invention using non-processive endonucleases for DNA isolation, segregate bacterial genomes away from specific PCR inhibitors. Table 21 provides a list of common interferents, the levels they were tested at in DpnI segregations, and the resulting detection with and without DpnI segregation.

TABLE 21

Common PCR interferents tested

| Inhibitor | Concentration tested | Detection of input DNA pre-enrichment | Detection of input DNA post-enrichment |
|---|---|---|---|
| Pollen | 10 mg/ml | 0% | 27% |
| Pollen | 100 mg/ml | 0% | 3% |
| Humic acid | 10 mg/ml | 0% | 17% |

FIG. 24 shows that when 150 pg of E. coli DNA is put into a 16S E. coli specific qPCR assay, it is 100% detected. Detection decreases to 0% as the level of rye pollen increases to approximately 10,000 ug/ml. The extraction of 150 ng of E. coli DNA was then tested in the presence of 10,000 ug/ml or 100,000 ug/ml rye pollen. In both cases, PCR inhibition was alleviated, restoring some level of E. coli detection.

In can be appreciated that altering the protocol from Example 2 by one familiar in the art, including the number or types of buffer washes, the addition of additives (EDTA, inactivators of inhibitor), or increasing the levels of DpnI (to alleviate competitive inhibition) would result in improvements to the method presented here.

It should be understood that the examples and explanations described herein are merely illustrative of embodiments of the current invention and are not intended to limit the methods or compositions described herein. All of the various aspects, embodiments, and options described herein can be combined in any and all variations. All publications, patents, and patent applications mentioned in this specification are herein incorporated by reference to the same extent as if each individual publication, patent, or patent application was specifically and individually indicated to be incorporated by reference.

As used herein, the terms "comprises," "comprising," "includes," "including," "has," "having," "contains," or "containing," or any other variation thereof, are intended to be non-exclusive or open-ended. Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

What is claimed is:

1. A method for enriching a target nucleic acid in a mixed sample containing the target nucleic acid and a non-target nucleic acid, comprising:

(i) digesting the mixed sample with a methylation-sensitive or methylation-dependent endonuclease that cleaves the target nucleic acid and not the non-target nucleic acid;

(ii) digesting the sample with an endonuclease; wherein the endonuclease cleaves the non-target nucleic acid and not the target nucleic acid, resulting in non-target nucleic acid ends that do not bind to the cleaved target nucleic acid;

(iii) circularizing the cleaved target nucleic acid; wherein the circularized target nucleic acid is resistant to digestion with DNase or exonuclease; and (iv) depleting the non-target nucleic acid.

2. The method of claim 1, wherein the circularized target nucleic acid of (iii) is resistant to digestion with Plasmid Safe DNase, Lambda exonuclease, Exonuclease V (RecBCD) or Exonuclease III.

3. The method of claim 1, wherein the endonuclease of (ii) is a restriction endonuclease that forms blunt ends on the non-target nucleic acid.

4. The method of claim 1, wherein a restriction endonuclease recognition sequence of the non-target nucleic acid is located within a restriction endonuclease recognition sequence of the target nucleic acid.

5. The method of claim 1, further comprising ligating a linker to the cleaved target nucleic acid, circularizing the cleaved target nucleic acid, and amplifying the target nucleic acid using a primer for the linker.

6. The method of claim 5, wherein the amplifying is performed by rolling circle amplification.

7. The method of claim 5, wherein the amplifying is performed by polymerase chain reaction.

8. The method of claim 5, wherein the amplifying is performed using Phi29 DNA polymerase.

9. The method of claim 1, wherein (i) and (ii) are performed simultaneously.

10. The method of claim 1, wherein (iv) is performed before (ii).

11. The method of claim 1, wherein the depleting is performed by gel isolation, size exclusion, or exonuclease digestion.

12. The method of claim 1, wherein the mixed sample contains less than 10 pg of target nucleic acid.

13. The method of claim 1, wherein the mixed sample further comprises humic acid, diesel soot, or an environmental or clinical contaminant.

14. The method of claim 1, wherein the mixed sample contains nucleic acid from at least two different prokaryotic organisms.

15. The method of claim 1, wherein the mixed sample contains nucleic acid from human and bacterial organisms.

16. The method of claim 1, wherein the mixed s, p e contains nucleic acid from eukaryotic and prokaryotic organisms.

17. The method of claim 1, wherein the mixed sample contains nucleic acid from an unknown organism.

* * * * *

UNITED STATES PATENT AND TRADEMARK OFFICE
CERTIFICATE OF CORRECTION

PATENT NO. : 10,190,113 B2
APPLICATION NO. : 15/782277
DATED : January 29, 2019
INVENTOR(S) : Forsyth Page 1 of 1

It is certified that error appears in the above-identified patent and that said Letters Patent is hereby corrected as shown below:

In the Claims

Column 44, Line 19, Claim 16, please delete "s, p e" and insert -- sample --

Signed and Sealed this
Twenty-first Day of April, 2020

Andrei Iancu
*Director of the United States Patent and Trademark Office*